(12) United States Patent
Heisel et al.

(10) Patent No.: US 10,625,044 B2
(45) Date of Patent: Apr. 21, 2020

(54) GUIDING MEDICAL DEVICES AND ASSOCIATED METHODS OF MANUFACTURING

(71) Applicant: St. Jude Medical, Atrial Fibrillation Division, Inc., St. Paul, MN (US)

(72) Inventors: Jennifer Marie Heisel, Princeton, MN (US); Gregory James Dakin, Edina, MN (US); Somally Mom, Savage, MN (US)

(73) Assignee: St. Jude Medical, Atrial Fibrilation Division, Inc., St. Paul, MN (US)

( * ) Notice: Subject to any disclaimer, the term of this patent is extended or adjusted under 35 U.S.C. 154(b) by 417 days.

(21) Appl. No.: 15/436,439

(22) Filed: Feb. 17, 2017

(65) Prior Publication Data
US 2017/0296777 A1 Oct. 19, 2017

Related U.S. Application Data

(62) Division of application No. 14/272,068, filed on May 7, 2014, now abandoned.
(Continued)

(51) Int. Cl.
*A61M 25/00* (2006.01)
*A61M 25/01* (2006.01)
(Continued)

(52) U.S. Cl.
CPC ......... *A61M 25/0012* (2013.01); *A61L 29/06* (2013.01); *A61M 25/005* (2013.01);
(Continued)

(58) Field of Classification Search
CPC ................................................ A61M 25/0012
See application file for complete search history.

(56) References Cited

U.S. PATENT DOCUMENTS

| 4,817,613 A | 4/1989 | Jaraczewski et al. |
| 6,241,744 B1 | 6/2001 | Imran et al. |
| (Continued) | | |

FOREIGN PATENT DOCUMENTS

| EP | 0839547 | 5/1998 |
| EP | 2465568 | 6/2012 |
| (Continued) | | |

OTHER PUBLICATIONS

International Search Report and Written Opinion for PCT/US2014/037124 dated Aug. 22, 2014.
(Continued)

*Primary Examiner* — Cachet I Proctor
(74) *Attorney, Agent, or Firm* — Wiley Rein LLP

(57) ABSTRACT

A catheter assembly includes an inner liner made of flexible material and an outer layer having a steering mechanism. A catheter assembly is provided that includes an inner liner made of flexible material, and an outer layer having a steering mechanism that includes at least one wire and a corresponding lumen for each of the at least one wire through which the respective wire may travel. The outer layer includes a braided wire assembly that includes at least two wires braided into a wire mesh, and further includes a see-through portion positioned proximate a pull wire extraction location to facilitate extraction.

9 Claims, 15 Drawing Sheets

Related U.S. Application Data

(60) Provisional application No. 61/820,545, filed on May 7, 2013.

(51) Int. Cl.

| | | |
|---|---|---|
| *A61L 29/06* | (2006.01) | |
| B29C 41/08 | (2006.01) | |
| B29C 41/22 | (2006.01) | |
| *A61B 18/14* | (2006.01) | |
| *A61B 18/00* | (2006.01) | |
| *A61B 90/00* | (2016.01) | |
| *B29K 77/00* | (2006.01) | |
| *B29L 31/00* | (2006.01) | |

(52) U.S. Cl.
CPC .... *A61M 25/0045* (2013.01); *A61M 25/0108* (2013.01); *A61M 25/0147* (2013.01); *B29C 41/08* (2013.01); *B29C 41/22* (2013.01); *A61B 18/1492* (2013.01); *A61B 2018/00357* (2013.01); *A61B 2018/00577* (2013.01); *A61B 2090/3966* (2016.02); *A61B 2218/002* (2013.01); *A61M 25/0009* (2013.01); *A61M 2025/0008* (2013.01); *A61M 2025/0046* (2013.01); *A61M 2025/015* (2013.01); *A61M 2205/583* (2013.01); *A61M 2210/125* (2013.01); *B29K 2077/00* (2013.01); *B29K 2995/007* (2013.01); *B29L 2031/7542* (2013.01)

(56) References Cited

U.S. PATENT DOCUMENTS

| | | |
|---|---|---|
| 2002/0169377 A1 | 11/2002 | Khairkhahan et al. |
| 2003/0050686 A1 | 3/2003 | Raeder-Devens et al. |
| 2003/0236492 A1 | 12/2003 | Honebrink |
| 2004/0111095 A1 | 6/2004 | Gordon et al. |
| 2004/0122360 A1* | 6/2004 | Waldhauser ...... A61M 25/0012 604/95.04 |
| 2004/0153049 A1 | 8/2004 | Hewitt et al. |
| 2007/0255255 A1 | 11/2007 | Shah et al. |
| 2008/0091169 A1* | 4/2008 | Heideman ......... A61M 25/0012 604/527 |
| 2008/0154190 A1 | 6/2008 | St. Germain et al. |
| 2009/0143633 A1 | 6/2009 | Edmundson et al. |
| 2010/0030114 A1 | 2/2010 | Nguyen et al. |
| 2012/0010490 A1* | 1/2012 | Kauphusman ....... A61B 5/0422 600/373 |

FOREIGN PATENT DOCUMENTS

| | | |
|---|---|---|
| EP | 2471480 | 7/2012 |
| WO | 136981 | 11/2007 |
| WO | 068505 | 5/2012 |

OTHER PUBLICATIONS

International Search Report and Written Opinion for PCT/US2014/037137 dated Aug. 27, 2014.

* cited by examiner

GUIDING MEDICAL DEVICES AND ASSOCIATED METHODS OF MANUFACTURING

CROSS-REFERENCE TO RELATED APPLICATIONS

This application is a divisional of U.S. application Ser. No. 14/272,068, filed 7 May 2014, which claims the benefit of U.S. provisional application No. 61/820,545, filed 7 May 2013. The forgoing applications are hereby incorporated by reference as though fully set forth herein.

BACKGROUND

The present disclosure is generally related to medical devices useable in the human body. More particularly, the present disclosure is directed to steerable introducers, catheters or other medical devices capable of facilitating delivery of and/or access of other medical devices therethrough.

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart or other organ. The catheter may carry one or more electrodes, which may be used for ablation, diagnosis, or the like. Such medical devices may instead or additionally facilitate the delivery of other devices to targeted locations within the body.

To facilitate placement of catheters or other medical devices at a location of interest within the patient, it may be introduced through another catheter, often referred to as a "guiding catheter," "introducer catheter" "introducer," "sheath," or the like, and the terms may be used interchangeably herein. Generally speaking, an introducer generally refers to a tube that may be used to place other catheters or medical devices into specific areas of the body. In some cases, the introducers may be steerable, and used to place catheters and/or other medical devices that have little or no directional control, into specific areas of the patient's body.

Generally, an introducer would have an overall outside diameter small enough to negotiate blood vessels or other anatomy while retaining an inner diameter ("bore size") large enough to accommodate the medical device therethrough. Furthermore, since the path within the patient may be long, tortuous, and/or involve intricate placement of another medical device(s), maneuverability via steering the introducer may be particularly beneficial. Steerability may involve steering mechanisms, that can be difficult to manufacture while maintaining desired yields.

SUMMARY

In accordance with one embodiment, a catheter assembly is provided that includes an inner liner made of flexible material, and an outer layer having a steering mechanism that includes at least one wire and a corresponding lumen for each of the at least one wire through which the respective wire may travel. The outer layer includes a braided wire assembly that includes at least two wires braided into a wire mesh, and further includes a see-through portion positioned proximate a pull wire extraction location to facilitate extraction.

In accordance with one embodiment, a catheter assembly is provided that includes an inner liner made of flexible material, and an outer layer having a steering mechanism that includes at least one wire and a corresponding lumen for each of the at least one wire through which the respective wire may travel. The outer layer includes a braided wire assembly that includes at least two wires braided into a wire mesh, where the braided wire assembly is braided in a substantially consistent braid pattern over its length.

In accordance with one embodiment, a catheter assembly is provided that includes an inner liner made of flexible material, and an outer layer having a steering mechanism that includes at least one wire and a corresponding lumen for each of the at least one wire through which the respective wire may travel. The outer layer includes a braided wire assembly that includes at least two wires braided into a wire mesh, where the outer layer comprises a plurality of segments of decreasing durometer from proximal end to distal end.

In accordance with another embodiment, a method of manufacturing a catheter is provided. The method includes providing a mandrel, placing a lining material over the mandrel to form an inner liner, placing a thermoplastic elastomer layer over the inner liner, at least along the mandrel at a location where one or more pull wires will be extracted, providing at least one pull wire, placing a flexible liner over each of the at least one pull wires to create at least one lumen, placing a braided wire assembly over the inner liner and the at least one flat lumen in a consistent braid pattern where the braided wire assembly includes at least two wires braided into a wire mesh, providing pull wire access areas in the braided wire assembly, covering the braided wire assembly with one or more melt processing polymers having decreasing durometers from proximal to distal end of the mandrel, covering a portion of the braided wire assembly proximate the location where the one or more pull wires will be extracted with a melt processing polymer that is substantially see-through, applying sufficient heat to the one or more melt processing polymers and the see-through melt processing polymer to raise the temperature of the polymer above its melting point, cooling the assembly, and removing the mandrel to form a catheter.

In accordance with another embodiment, a method of manufacturing a catheter is provided. The method includes providing a mandrel, placing a lining material over the mandrel to form an inner liner, placing a thermoplastic elastomer layer over the inner liner at least along the mandrel at a location where one or more pull wires will be subsequently be extracted, providing at least one pull wire, placing a flexible liner over each of the at least one pull wires to create at least one lumen, placing a braided wire assembly over the inner liner and the at least one lumen where the braided wire assembly includes at least two wires braided into a wire mesh, covering the braided wire assembly with a melt processing polymer, applying sufficient heat to the melt processing polymer to raise the temperature of the polymer above its melting point, cooling the assembly, and removing the mandrel to form a catheter.

In accordance with another embodiment, a method of manufacturing a catheter is provided. The method includes providing a mandrel, placing a lining material over the mandrel to form an inner liner, providing at least one wire, placing a flexible liner over each of the at least one wires to create at least one lumen, placing a braided wire assembly over the inner liner and the at least one lumen consistent braid pattern where the braided wire assembly includes at least two wires braided into a wire mesh, covering the braided wire assembly with a melt processing polymer, applying sufficient heat to the melt processing polymer to raise the temperature of the polymer above its melting point, cooling the assembly, and removing the mandrel to form a catheter.

In accordance with another embodiment, a method of manufacturing a catheter is provided. The method includes providing a mandrel, placing a lining material over the mandrel to form an inner liner, providing at least one wire, placing a flexible liner over each of the at least one wires to create at least one lumen, placing a braided wire assembly over the inner liner and the at least one lumen, the braided wire assembly including at least two wires braided into a wire mesh, covering the braided wire assembly with one or more melt processing polymers having decreasing durometers from proximal to distal end of the mandrel, applying sufficient heat to the melt processing polymers to raise the temperature of the polymer above their melting point, cooling the assembly, and removing the mandrel to form a catheter.

In accordance with another embodiment, a method of manufacturing a catheter is provided. The method includes providing a mandrel, placing a lining material over the mandrel to form an inner liner, providing at least one pull wire, placing a flexible liner over each of the at least one wires to create at least one lumen, placing a braided wire assembly over the inner liner and the at least one lumen, the braided wire assembly including at least two wires braided into a wire mesh, providing pull wire access areas in the braided wire assembly towards a proximal end of the mandrel, covering the braided wire assembly with a melt processing polymer, covering a portion of the braided wire assembly proximate the location where the one or more steering wires will be extracted with a melt processing polymer that is substantially see-through, applying sufficient heat to the one or more melt processing polymers and the see-through melt processing polymer to raise the temperature of the polymer above its melting point, cooling the assembly, and removing the mandrel to form a catheter.

DETAILED DESCRIPTION

The disclosure sets forth improved steerable introducers, catheters, and/or other medical devices that facilitate passage of one or more other medical devices therethrough, where improved manufacturing materials, mechanisms and/or techniques enhance quality and cast a wider net of collaborative medical devices.

Figure 1:
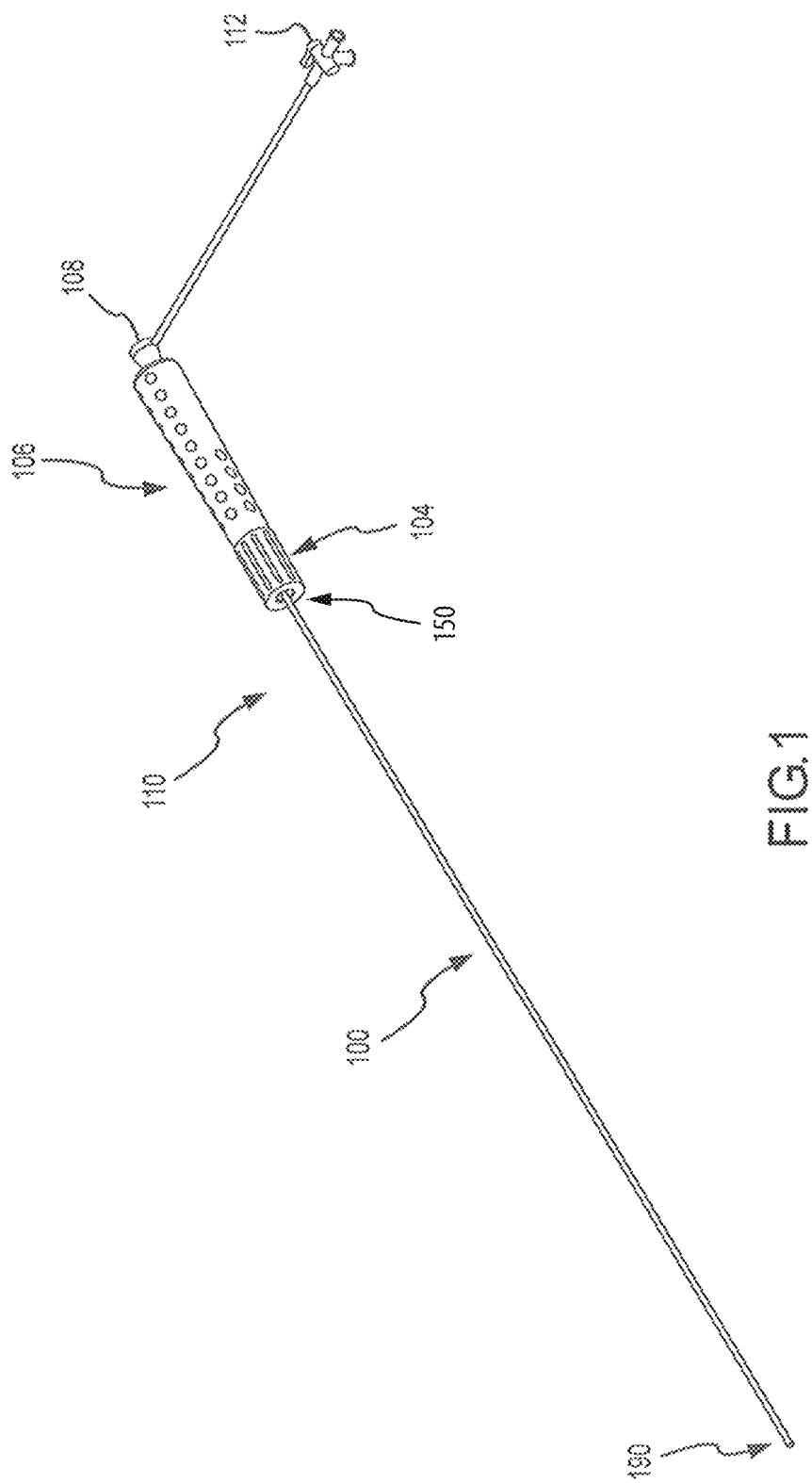
FIG. 1 is perspective view of an embodiment of an introducer or catheter in which the principles described herein may be implemented.

FIG. 1 is a perspective view of a catheter assembly or introducer assembly 110 according to one embodiment including a catheter or an introducer 100 having a proximal portion 150 and a distal portion 190. The introducer 100 may be operably connected to a handle assembly 106 which assists in guiding or steering the introducer during procedures. The introducer 110 further includes a hub 108 operably connected to an inner lumen (not shown) within the handle assembly 106 for insertion or delivery of catheter assemblies, fluids, or any other devices known to those of ordinary skill in the art. Optionally, the catheter assembly 110 further includes a valve 112 operably connected to the hub 108.

Figure 2:
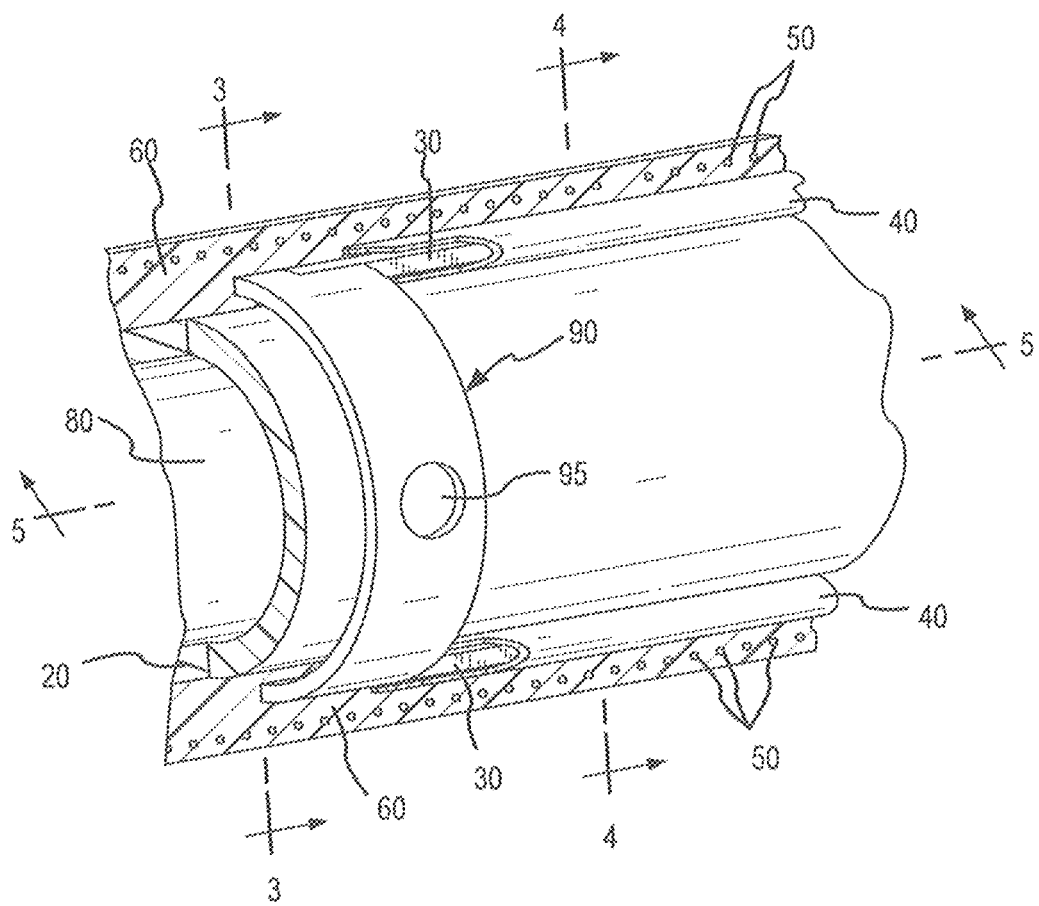
FIG. 2 illustrates a perspective view of a section of an introducer according to one embodiment, cut away to show details.

FIG. 2 illustrates a perspective view of an exemplary introducer, cut away to show details. An exemplary method of manufacture of introducer 100 according to a representative embodiment will be described with reference to FIGS. 2, 3, 4, 6, 7 and 8. As they are assembled, the introducer components may be collectively referred to as an introducer assembly or a catheter assembly.

Inner liner 20 may be an extruded polytetrafluoroethylene (PTFE) tubing, such as TEFLON® brand tubing, which is available commercially. Inner liner 20 may also be made of other melt processing polymers, including, without limitation, etched polytetrafluoroethylene, polyether block amides, nylon and other thermoplastic elastomers. Once such elastomer is PEBAX®, made by Arkema, Inc. PEBAX of various durometers may be used, including, without limitation, PEBAX 30D to PEBAX 72D. In one embodiment, inner liner 20 is made of a material with a melting temperature higher than that of an outer layer 60, which will be further described below, such that inner liner 20 will withstand melt processing of outer layer 60.

A wire 30 is placed longitudinally along inner liner 20. The wire 30 may be any shape or configuration, and is depicted as a flat wire in the illustrated embodiment. For purposes of this description, a "flat wire" or a "flat pull wire" generally refers to a wire that is characterized by a cross-section that, when measured along two orthogonal axes, is substantially flat. A flat wire typically has a rectangular cross-section. For example, the rectangular cross-section may be approximately 0.004"×0.012". The cross-section need not be perfectly rectangular. For example, the present invention contemplates a cross-section of the flat wire may be oval, provided that the overall cross-section is generally flat. For example, a wire may be properly characterized as a flat wire if it has a cross-section that is measured X in one direction and greater than X in a second direction (e.g., at least 3×) generally orthogonal to the first direction. A wire whose cross-section is substantially I-shaped may also be a flat wire if, generally, its height is substantially greater than its width at its widest measurement. One of ordinary skill will appreciate that a flat wire may be defined in the context of the overall teachings of this application.

Flat wire 30 may be constructed of stainless steel and may be about 0.002" by about 0.016", or about 0.004" by about 0.012." In one embodiment, at least a portion of flat wire 30 is encased inside another preformed tube 40 before placement along inner liner 20 to form a flat lumen 42. Preformed tube 40 need not have the same shape as the cross-section of flat wire 30, but instead may be round, oval, rectangular, or another like shape. Preferably, preformed tube 40 has a cross-section that is not the same shape as the cross-section of flat wire 30 in order to facilitate movement of flat wire 30 in preformed tube 40. Preformed tube 40 may be formed of polytetrafluoroethylene, polyether block amides, nylon, other thermoplastic elastomers, or another substance. Preferably, preformed tube 40 has a higher melting point than outer layer 60, which will be further described below, so that preformed tube 40 will not melt when outer layer 60 is subjected to melt processing.

In alternative embodiments, flat wire 30 may be covered with lubricious materials including silicone, TEFLON®, siloxane, and other lubricious materials (not shown), before placement. Alternatively, flat wire 30 may also be coated with a lubricious layer to promote slidability. It is also contemplated that flat wire 30 may be manufactured with a smooth surface to promote slidability. While stainless steel is a preferred material from which to compose flat wire 30, other materials may be used, including, without limitation, materials that are used for conventional round pull wires.

More than one flat wire 30 may also be used. In such cases, each such flat wire 30 may be encased inside its own flexible tube 40 to form separate flat lumens 42. Preferably, a pair of flat wires 30 are used, spaced apart about 180 degrees about the circumference of inner liner 20. Although still additional wires 30 may additionally be used to realize additional deflection directions.

In one embodiment, outer layer 60 is placed over inner liner 20, flat wires 30, and preformed tube 40 forming flat lumen 42. Outer layer 60 may be made of either single or multiple sections of tubing that may be either butted together or overlapped with each other. In one embodiment, outer layer 60 is an extruded polytetrafluoroethylene tubing, such as TEFLON® brand tubing, which is available commercially. Outer layer 60 may also be made of other melt processing polymers, including, without limitation, etched polytetrafluoroethylene, polyether block amides, nylon and other thermoplastic elastomers. Once such elastomer is PEBAX® made by Arkema, Inc. PEBAX of various durometers may be used, including, without limitation, PEBAX30D to PEBAX 72D. Outer layer 60 may also comprise more than one layer, including for example two or more tubes of a melt processing polymer.

Optionally, a braided wire assembly 50 may be placed over inner liner 20 and any flat wires 30 before outer layer 60 is applied. Braided wire assembly 50 may be formed of stainless steel wire, including for example 0.003" high tensile stainless steel wire. Braided wire assembly 50 may be formed in a standard braid pattern and density, for example, about 16 wires at about 10 to about 60 pics per inch ("PPI") density. These and other consistent braid patterns may be used in connection with the described (and analogous) introducers or other guiding medical devices and described herein.

Alternatively, a braid may be used that is characterized by a varying braid density. More particularly, the outer diameter of the introducer may be minimized at the distal tip by an improved braided wire assembly, such as the use of a braid that is characterized by a varying braid density from the proximal end to the distal tip. In one embodiment, the braid is less dense at the tip than at the proximal end of the catheter. Some applications may be better suited if the braid density is more dense at the tip than at the proximal end, while other applications may be better suited if the braid density is greater on both ends than in the middle of the catheter. Thus, for example, braided wire assembly 50 may be characterized by a first braid density at proximal end 150 of introducer 100 and then transition to one or more different braid densities as braided wire assembly 50 approaches distal end 190 of introducer 100. The braid density of distal end 190 may be greater or less than the braid density at proximal end 150. In one example, the braid density at the base (i.e., proximal end 150) is about 50 PPI and the braid density at distal end 190 is about 10 PPI. In another embodiment, the braid density at distal end 190 is about 20% to about 35% of the braid density at the base/proximal end 150. In another example, the braid density at proximal end 150 is about 10 PPI and the braid density at distal end 190 is about 50 PPI, or the braid density at proximal end 150 is about 20% to about 35% of the braid density at distal end 190.

Figure 6:
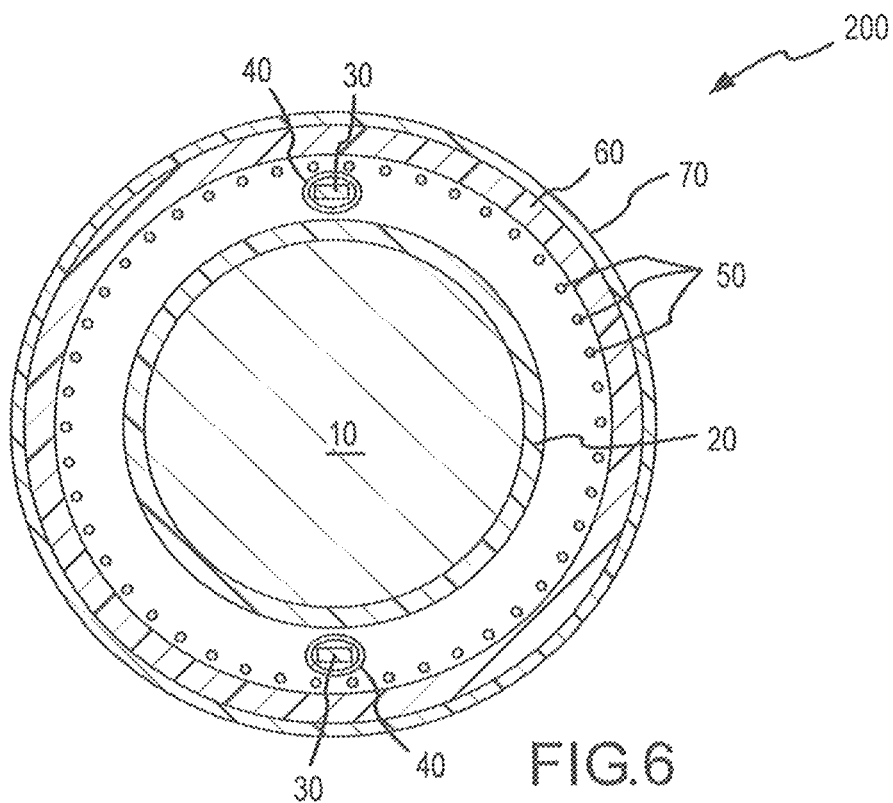
FIG. 6 is a representative cross-sectional view of an introducer assembly prior to the application of heat to melt process the outer layer.

As depicted in FIG. 6, the representative mandrel 10 is round in cross-section in the illustrated embodiment, and may range from, for example, about 6 inches to about 4 feet or more in length. The mandrel 10 may represent a component of the introducer assembly 200, and may be the first component thereof during manufacture of introducer 100. Mandrel 10 has a distal end and a proximal end. In one embodiment, the manufacturing process begins by placing an inner liner 20 on mandrel 10. Inner liner 20 may be knotted at one end (e.g. the distal end) and then fed onto mandrel 10.

In one embodiment, and as noted above, the introducer 100 may include a high pic-per-inch (PPI) at the distal end to aid with deflection, while using a lower PPI in the body which lowers material costs. This can be accomplished by pulling the braid tight onto a reflow mandrel 10 having a diameter to match the French size of the finished introducer. This diameter may be smaller than the braiding mandrel, and once the braid is pulled down tight on the reflow mandrel, there may be little difference between the high PPI and low PPI areas. In cases where the difference does not warrant additional complexity to the build or risk to the yield by cutting the braid at specific locations to accommodate the differing PPI and properly orienting it on the reflow mandrel, a continuous braid PPI may be used on the braid mandrel. As one representative example, a substantially consistent braid pattern having approximately 18-21 PPI on the mandrel 10 may be utilized. Using a continuous braid PPI over the length of braiding enables the braid to be cut from anywhere on the reflow mandrel or elsewhere. For example, the braid can be pulled down tightly on a reflow mandrel to provide one continuous PPI, and therefore orientation on the mandrel is not an issue. Further, an easier process may lead to less "scrap" and therefore higher yields. Thus, in some cases, benefits of using a consistent braid pattern may include reduced scrap cost, reduced production time, potentially reduced part-to-part variability since the braid used throughout the sheath is the same (PPI) versus variable and operator dependent, etc.

Braided wire assembly 50 may be formed separately on a mandrel or disposable core. One or more portions of braided wire assembly 50 may be heat tempered and cooled before incorporation into catheter assembly 200 though methods that are known to those of ordinary skill. The action of heat tempering may help to release the stress on the wire and help reduce radial forces.

FIG. 6 displays a cross-section of catheter assembly/introducer assembly 200 having two flat wires 30 and braided wired assembly 50 encompassed by outer layer 60 before lamination of the materials by heating. In one embodiment, a layer of heat shrink 70 is placed over the top of outer layer 60 as depicted in FIG. 6. Heat shrink 70 may be, for example, a fluoropolymer or polyolefin material.

Figure 7:
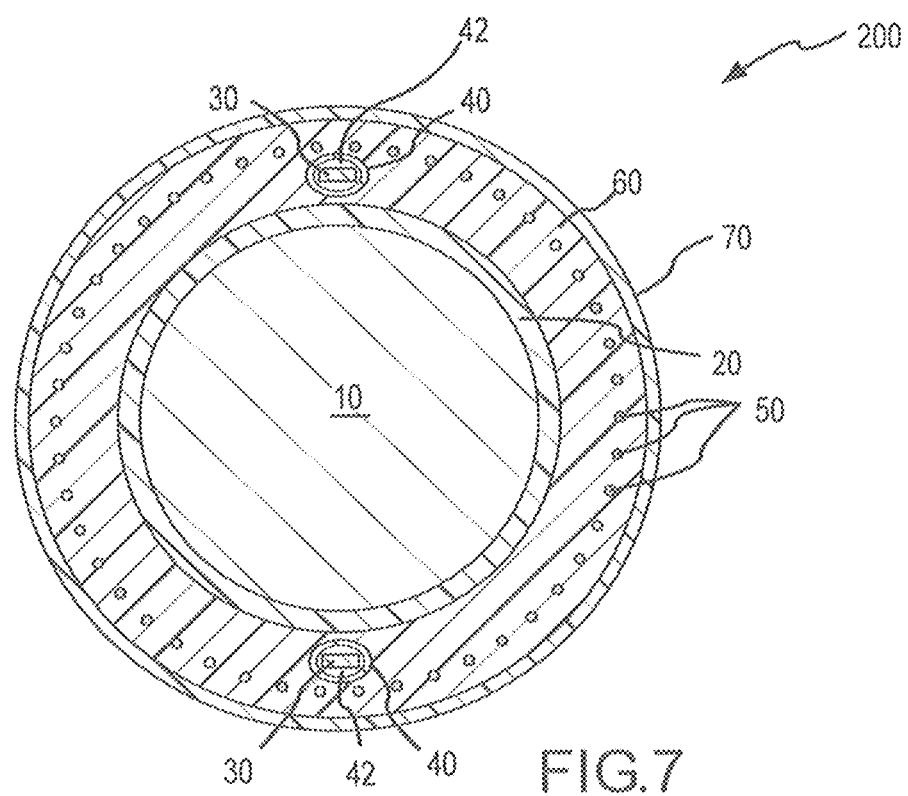
FIG. 7 is a representative cross-sectional view of an introducer after the application of heat to melt process the outer layer.

FIG. 7 depicts introducer assembly 200 after a lamination process. Catheter assembly 200 may be laminated by heating catheter assembly 200 until the material comprising outer layer 60 flows and redistributes around the circumference thereof as depicted in FIG. 7. Heat shrink 70 has a higher melting temperature than outer layer 60; and during the melt process, heat shrink 70 retains its tubular shape and forces the liquefied outer layer 60 material into braided wire assembly 50 (if present) and into contact with tubes 40 and inner liner 20. Introducer assembly 200 may then be cooled. In FIG. 7, mandrel 10 is still in place.

Figure 4:
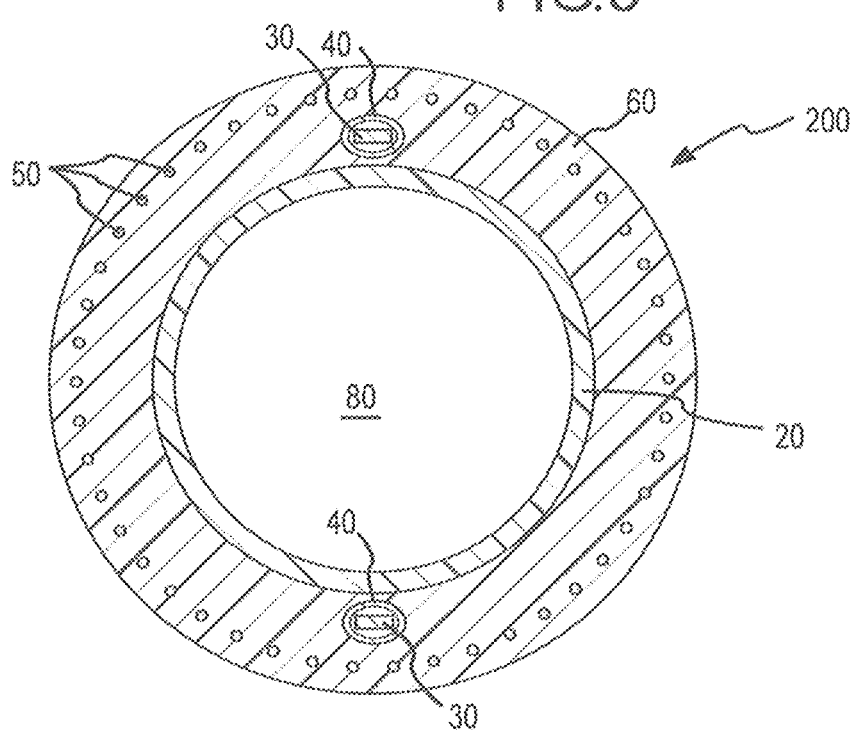
FIG. 4 is a representative cross-sectional view taken along line 4-4 in FIG. 2.

Mandrel 10 may be removed from introducer assembly 200, leaving behind a lumen 80 as illustrated in FIG. 4, which depicts an introducer 100 made in accordance with representative methods described herein following the application of heat for the lamination process. Optionally, heat shrink 70 may be left in place around outer layer 60, as depicted in FIG. 7, even after mandrel 10 is removed.

Figure 3:
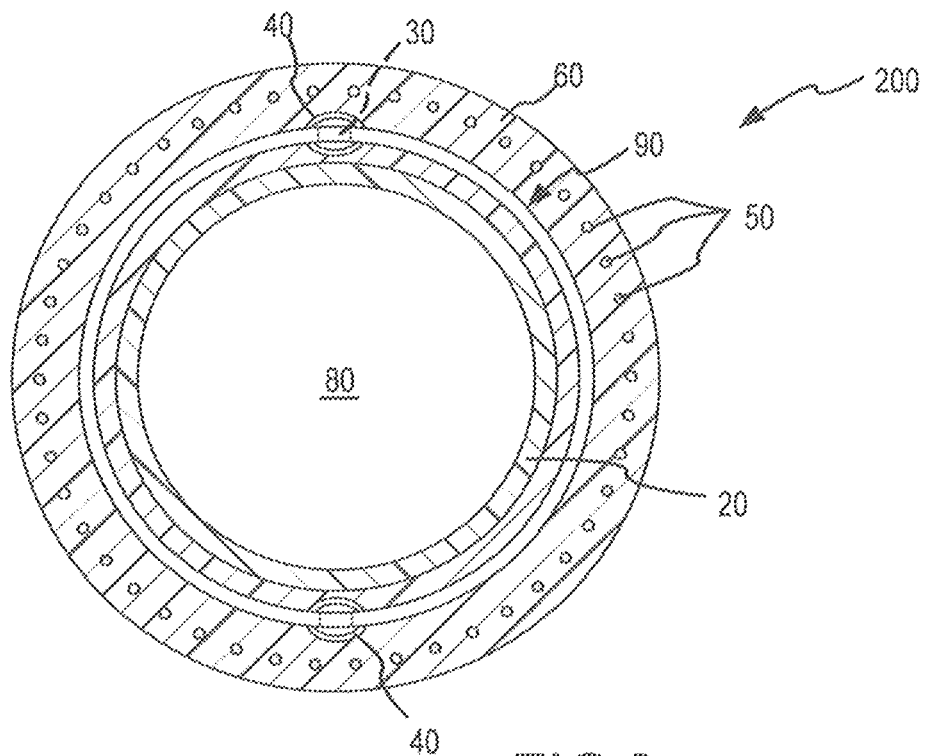
FIG. 3 is a representative cross-sectional view taken along line 3-3 in FIG. 2.
Figure 8:
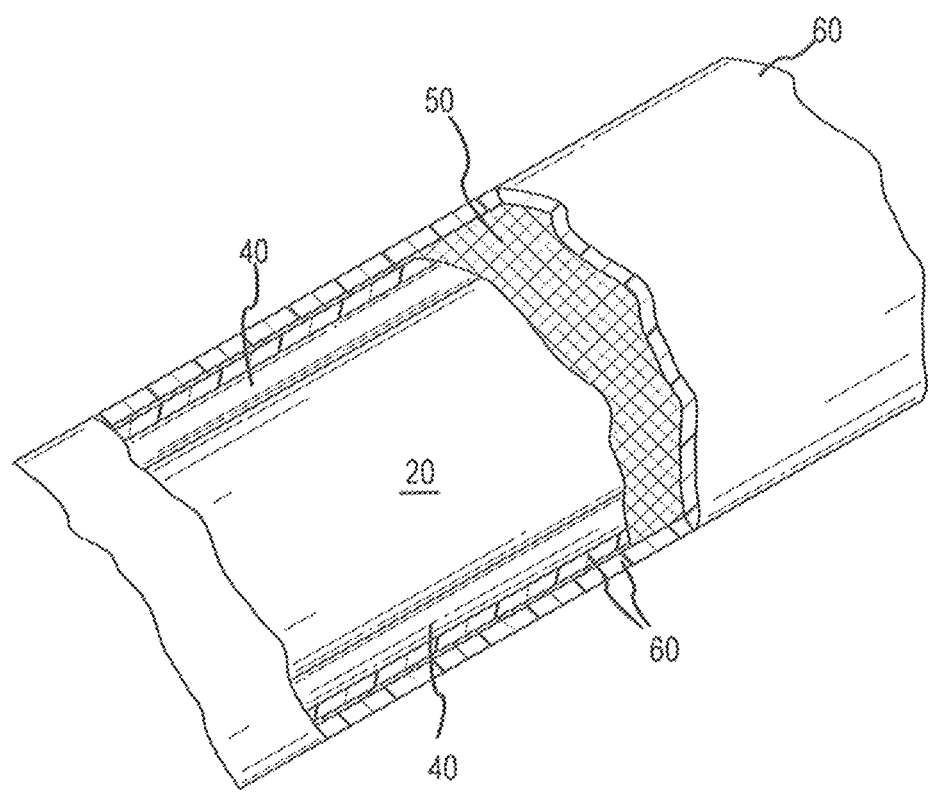
FIG. 8 illustrates a perspective view of a partially assembled representative introducer in accordance with another embodiment, cut away to show details.

If heat shrink 70 is removed, outer layer 60 becomes the outermost layer of catheter 100. The result is a substantially circular introducer 200 with pull wires 30 embedded within outer layer material as illustrated in FIGS. 3 and 4. FIG. 3 is a cross-sectional view taken at the point of a pull ring 90 as depicted in FIG. 2, while FIG. 4 is a cross-sectional view taken at a point proximal to pull ring 90. FIG. 8 is a perspective view of catheter assembly 200, cut away to show certain details of construction.

Introducer assembly 200 may be manufactured using alternative techniques. In one embodiment, introducer assembly 200 may be formed by extruding outer layer 60 over inner layer 20 and braid wire assembly 50. In another embodiment, introducer assembly 200 may formed by using a combination of heat and a press that has a mold for defining the final shape of catheter 100. Still other variations on representative manufacturing processes are described below.

Introducer 100 formed using the methods described herein may have varying sizes and various uses. For example, introducer 100 may be used in atrial fibrillation cases as well as atrial tachycardia cases. In connection with certain heart applications, catheter 100 manufactured using the improvements discussed herein is preferably less than about 12 French outer diameter, and more preferably less than about 10 French outer diameter. For use as a steerable introducer, an outer diameter of approximately 11 French may be suitable. In other embodiments, the inner diameter may be from about 10 to 16 French when the introducer 100 is used to deliver devices such as left atrial appendage occluders. Indeed, by using flat wires to form braided wire assembly 50, one can achieve very thin-walled shafts 100, allowing for larger lumen sizes for given outside dimensions.

In another embodiment, construction of introducer 100 may be modified to utilize materials of various durometer hardness (as measured, for example, using a Shore durometer hardness scale). For example, proximal end 150 of introducer 100 may be made of a material such as nylon 11, and the remainder of introducer 100 may be made of one or more PEBAX materials. In one embodiment, the durometer hardness levels will decrease as introducer 100 shaft approaches distal end 190. For example, a nylon base may then be followed by one or more of the following PEBAX segments: 72D PEBAX; 63D PEBAX; 55D PEBAX; 40D PEBAX; 35D PEBAX; 30D PEBAX. Introducer 100 may also use one or more blends of the foregoing PEBAX materials, including for example, a 70D/63D PEBAX blend made by co-extrusion, or a 40D/35D PEBAX blend made by co-extrusion, or a 72D/63D PEBAX blend made by co-extrusion. In one embodiment, introducer 100 made with one or more segments of varying durometers will be reflowed together during manufacturing. The length of the segments may vary. Proximal end 150 of catheter 100 may be the longest segment, and more distal segments may vary between (for example) about 0.25" to about 6", or possibly from about 0.25" to about 3". The hardness levels of the segments and the lengths of the segments may be adjusted for specific applications, and preferably, the distal tip segment may have the lowest durometer of all segments. The segments may be selected to optimize shaft flexibility and torque delivery for the specific application.

In one embodiment, PEBAX is used rather than nylon 11 for the proximal shaft for purposes of flexibility. In another embodiment, an additional portion of the distal end is made from a lower durometer PEBAX than one or more segments positioned proximally along the shaft. For example, in one particular embodiment, an additional six inches of a lower durometer PEBAX is added to the distal end of the shaft for shaft compatibility when, for example, tracking through the heart to the left atrial appendage for safety concerns. Thus, in one embodiment, using different durometer configurations enables shaft integrity and steerability to be maintained throughout the shaft while having a softer flexible distal portion to prevent damage to the heart. The lower durometer portion at the distal end may be positioned at the distal portion of the proximal shaft yet prior to a most distal segment that includes a tip, or may be positioned as the last segment including distal tip itself.

Figure 5:
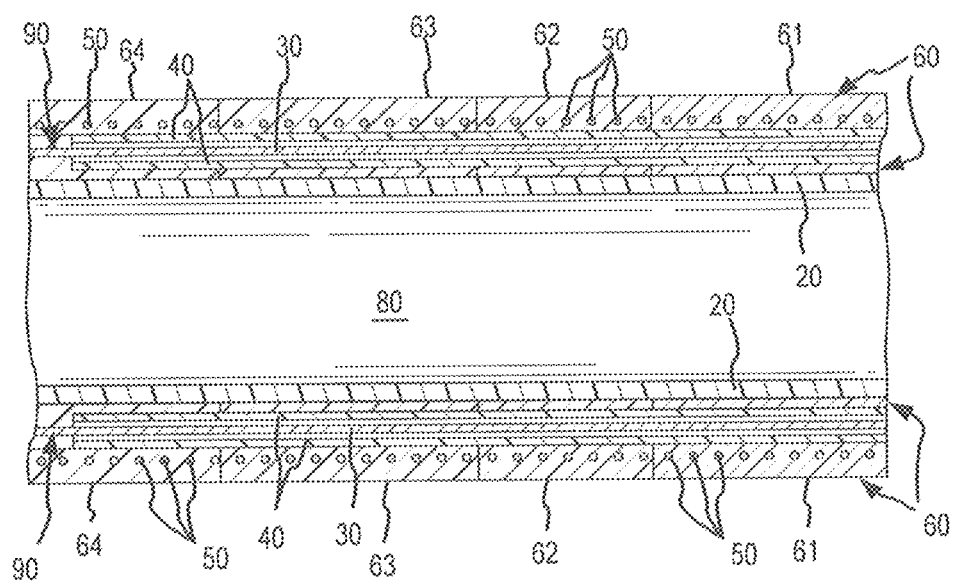
FIG. 5 is a representative cross-sectional view taken along line 5-5 in FIG. 2.

FIG. 5 illustrates another embodiment in which outer layer 60 is composed of multiple segments 61, 62, 63, 64, each of which has different material properties, such as degree of hardness, stiffness, or tensile strength. In one embodiment, segment 61 has the greatest degree of hardness; segments 62, 63, and 64 are more flexible than segment 61; segments 63 and 64 are more flexible than segments 61 and 62; and finally, segment 64 is more flexible than each of segments 61, 62 and 63. The number of segments may vary, as well as the relative lengths of the segments. In another representative embodiment, a more proximal portion such as portion 61 may be more flexible than an adjacent portion immediately distal to the portion 61. In yet other embodiments, the more proximal portion 61 may be more flexible than a plurality of the portions more proximal thereto.

In yet another embodiment, a modified braided wire assembly 50 is inserted between inner liner 20 and outer layer 60. Braided wire assembly 50 may be designed to have transitional braid densities starting at one braid density and transitioning to a lower braid density. In one embodiment, the braid may begin at a braid density of about 50 to about 60 PPI, or between about 50 and about 55 PPI, and then transition to a braid density at the tip of about 5 to about 20 PPI, or in other examples between about 5 to about 15 PPI. In another embodiment, the braid may begin at a braid density of about 5 to about 20 PPI and then transition to a braid density at the tip of about 50 to about 60 PPI. The braid density may transition slowly, or it may change using one or more segments. For example, there may be an intermediate zone with a braid density of about 30 to about 45 PPI. Variations in the braid density of braided wire assembly 50 may be used to increase or decrease flexibility of catheter 100 depending on the desired application.

Figure 9:
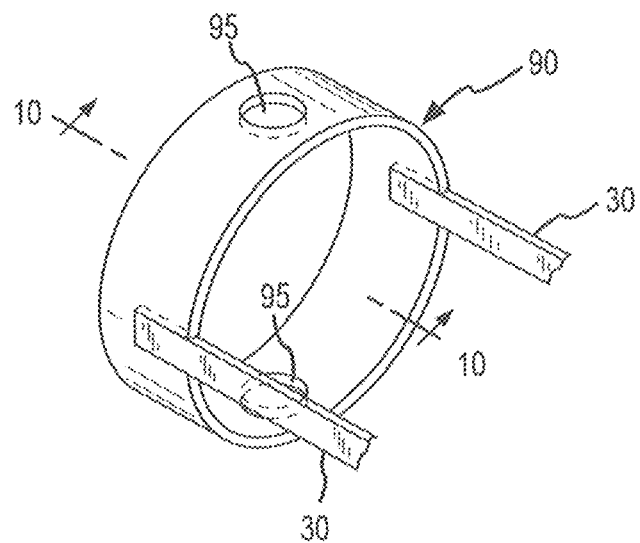
FIG. 9 illustrates a representative pull ring that may be used in an introducer in which the principles described herein may be implemented.
Figure 10:
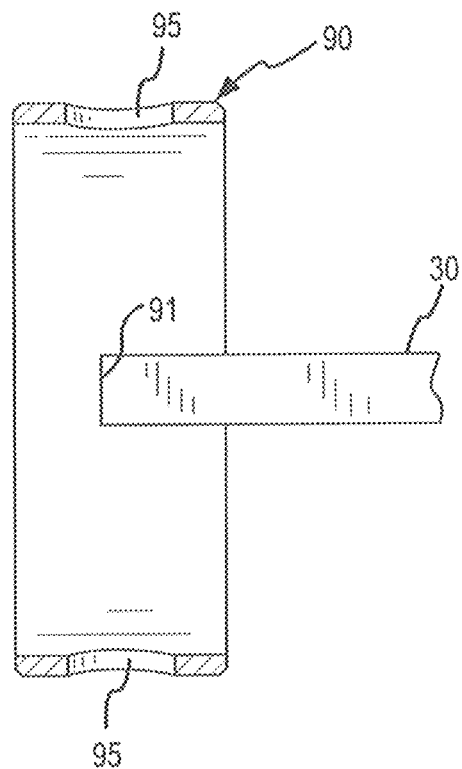
FIG. 10 is a sectional view of the pull ring of FIG. 9 taken along line 10-10.

In another embodiment, pull ring 90 is utilized to provide steerability. FIGS. 9 and 10 illustrate a preferred embodiment for pull ring 90. Pull ring 90 is a generally circular band with a cross-sectional shape (measured orthogonally to a tangential line relative to the circle of the band) that is substantially rectangular. The rectangular cross-section is more clearly depicted in FIG. 10. The outer dimension of pull ring 90 is preferably determined based on the application for catheter 100 to be manufactured. In one embodiment, pull ring 90 is about 0.10" in diameter.

Pull ring 90 may have at least one slot 91 that is configured to accommodate flat pull wire 30. Flat pull wire 30 may be secured within slot 91 by any technique that is appropriate given the materials of pull ring 90 and flat or other shaped pull wires 30. Acceptable techniques may include, but are not limited to, laser welding and/or other welding and bonding techniques.

In another embodiment, pull ring 90 may include one or more flow holes 95 as illustrated in FIGS. 9 and 10. During a melting process, the material of outer layer 60 melts and flows through flow holes 95. Upon cooling, the material of outer layer 60 bonds to pull ring 90 to provide better adhesion between pull ring 90 and the remaining components of catheter assembly 200, thereby improving performance of catheter 100. While flow holes 95 are depicted as circular, other shapes may be used. In one embodiment, pull ring 90 includes two 0.025" flow holes 95 spaced about 180 degrees apart around the circumference of pull ring 90. The size and shape of flow holes 95 may be adjusted based on the materials being used to form inner liner 20 and/or outer layer 60.

In another embodiment, pull ring 90 is utilized with non-flat pull wires. Pull ring 90 of this embodiment may utilize a circular band with a cross-sectional shape (measured orthogonally to a tangential line relative to the circle of the band) that is substantially rectangular. Pull ring 90 may have at least one slot that is configured to accommodate a non-flat pull wire (such as a round wire). Preferably, the tip of the non-flat pull wire is tapered to facilitate joinder with pull ring 90. The non-flat pull wire may be secured within the slot by any technique that is appropriate given the materials of pull ring 90 and the pull wires. Acceptable techniques may include, but are not limited to, laser welding and/or other welding and bonding techniques. In one embodiment, the non-flat pull wire is located within a preformed tube 40. Preformed tube 40 need not be the same shape as the cross-section of the pull wire, but instead, may be round, oval, rectangular, or another like shape. Preformed tube 40 may have, for example, a cross-section that is not the same shape as the cross-section of the pull wire in order to facilitate movement of the pull wire in the preformed tube. Preformed tube 40 may be formed of polytetrafluoroethylene, polyether block amides, nylon, other thermoplastic elastomers or another substance. In one embodiment, preformed tube 40 has a higher melting point than outer layer 60 so that the preformed tube will not melt when outer layer 60 is subjected to melt processing. In alternative embodiments, the pull wire may be covered with lubricious materials, such as silicone and other lubricious materials, before placement. Alternatively, the pull wire may be coated with a lubricious layer to promote slidability, and it is also contemplated that the pull wire may be manufactured with a smooth surface to promote slidability. While stainless steel is a preferred material to compose the pull wire, other materials may be used, including, without limitation, materials that are used for conventional pull wires.

Pull ring 90 is typically utilized near distal end 190 of introducer 100, but it is anticipated that pull ring 90 may be located at any position along introducer 100. Moreover, more than one pull ring 90 may be utilized in the same catheter 100. In one embodiment of catheter 100, two separate pull rings 90 may be utilized, each of which has its own flat pull wires 30 connected thereto.

Although multiple embodiments have been described above with a certain degree of particularity, those skilled in the art could make numerous alterations to the disclosed embodiments without departing from the teachings set forth herein. For example, pull ring 90 may be made of stainless steel or other materials, including, without limitation, materials that are used to form conventional pull ring assemblies. In addition, braided wire assembly 50 may be made of stainless steel or other materials, including materials that are used to form conventional braided wire assemblies.

The present disclosure further describes a torque transfer layer using braided flat wires for a catheter, and a large bore introducer catheter. For purposes of description, certain embodiments are described in connection with a flat wire guided, or steerable, introducer catheter. It is contemplated, however, that the described features may be incorporated into any number of catheters or introducers as would be appreciated by one of ordinary skill in the art. The large bore introducer catheter includes a combination of components and may be manufactured by either a reflow process or an extrusion process, allowing for introducer catheters having an internal diameter of at least about 6 F while maintaining the desirable improved properties of pushability, torqueability, and flexibility, for outer diameters of sufficient size for navigation of cardiac vasculature.

Figure 11:
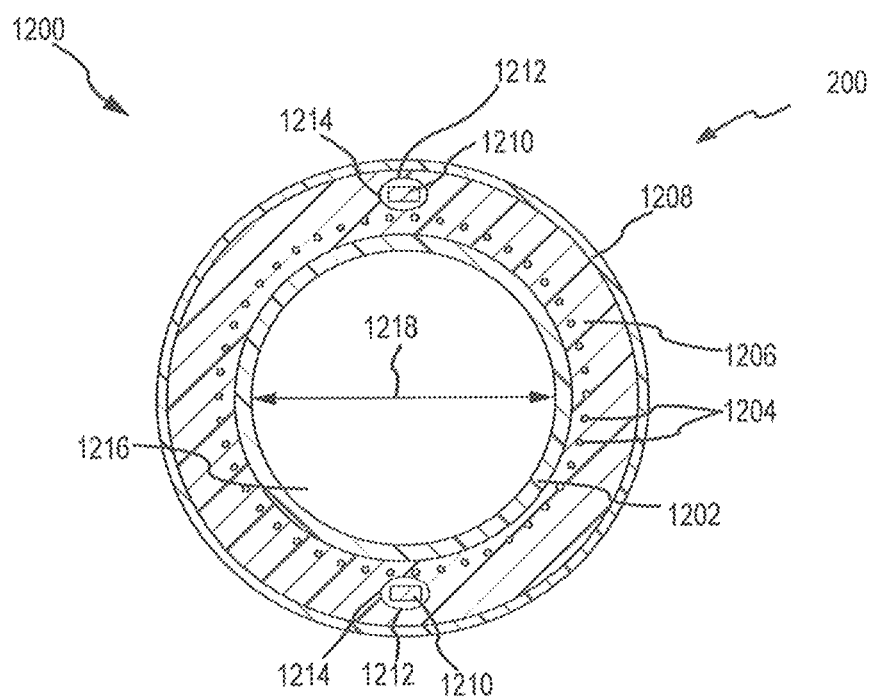
FIG. 11 is a representative cross-sectional view of a steerable, large bore introducer in accordance with another embodiment.

FIG. 11 depicts a cross-sectional view of an introducer catheter 1200 in accordance with a representative embodiment. The illustrated introducer catheter 1200 comprises a tubular polymeric inner liner 1202, a torque transfer layer 1204, an outer sheath 1206 comprised of a melt-processing polymer, and a heat shrink layer 1208. In the instance where the introducer is a steerable introducer, the introducer catheter 1200 further includes at least one steering wire, such as flat wire 1210, disposed longitudinally along the length of the introducer catheter 1200. For purposes of this invention, a "flat wire" refers to a wire that is characterized by a cross-section that, when measured along two orthogonal axes, is substantially flat. A flat wire typically has a rectangular cross section, though the cross section need not be perfectly rectangular. For example, the present invention contemplates that a cross section of the flat wire may be oval, provided that the overall cross section is generally flat. As the term is used herein, a wire may be properly characterized as a flat wire if it has a cross section that is measured x in one direction and at least 2x in a second direction generally orthogonal to the first direction. A wire whose cross section is substantially I-shaped may also be a flat wire if, generally, its height is substantially greater than its width at its widest measurement. One of ordinary skill will appreciate that a flat wire may be defined in the context of the overall teachings of this application.

The at least one flat wire 1210 may be further encased inside another polymeric tubular member 1212 forming a lumen 1214 for housing the flat wire 1210. The introducer catheter according to this embodiment is manufactured by a reflow bonding process in which the components are individually fed over a mandrel as discussed in more detail below.

In one embodiment, the inner liner 1202 is a polymeric material, such as polytetrafluoroethylene (PTFE) or etched PTFE. The inner liner 1202 may also be made of other melt processing polymers, including, without limitation, polyether block amides, nylon and other thermoplastic elastomers. Once such elastomer is PEBAX® made by Arkema, Inc. PEBAX of various durometers may also be used, including without limitation, PEBAX 30D or less to PEBAX 72D or more. In one embodiment, the inner liner 1202 is made of a material with a melting temperature higher than the outer sheath 1206 such that the inner liner 1202 will withstand the melt processing of the outer sheath 1206.

Inner liner 1202 defines a lumen 1216 therethrough, having a diameter 1218 of, for example, at least about 6 French, or at least about 7 French, and in other embodiments a larger bore between about 10 French and about 24 French. However, in some embodiments, it is contemplated that lumen 1216 may have a diameter 1218 of up to about 32 French or more, such as between about 7 French and about 32 French.

A torque transfer layer 1204 may be disposed between the inner liner 1202 and the heat shrink layer 1208, more preferably between the outer sheath 1206 and the inner liner 1202. In the instance where the introducer is a steerable introducer utilizing, for example, at least one longitudinal wire 1210, the torque transfer layer 1204 may be disposed between the inner layer 1202 and the outer sheath 1206 or between the outer sheath 1206 and the heat shrink layer 1208. The torque transfer layer 1204 may be made of stainless steel (for example, 304 or 316) wire or other acceptable materials known to those of ordinary skill in the art.

The torque transfer layer 1204 may be formed of a braided wire assembly comprised of flat wires, such as stainless steel wires including, for example, high tensile stainless steel wires. The torque transfer layer 1204 may be formed in any number of known braid patterns, including one-over-one (involving at least two wires), two-over-two (involving at least four wires) crossover patterns, etc. The braided flat wires typically have a thickness of at least about 0.0005" and a width of at least about 0.003". Examples of larger sizes include 0.001"×0.005" and 0.002"×0.006". For lumen diameters of at least about 6 French, braided flat wires of at least about 0.003" thick by at least about 0.007" wide, which heretofore were not used to form a wire mesh for the torque transfer layer, have produced surprisingly good results of increased pushability, torqueability, flexibility, and kink resistance over non-flat wires and smaller flat wires. In general, the individual wires have a ratio of width to the thickness of at least about 2:1, including, for example, 2:1 to 5:1. Flat wires of about 0.004" thick by about 0.012" wide and of about 0.004" thick by about 0.020" wide have also been braided with success to form torque transfer layers of superior performance.

The braid density, commonly measured in pixels per inch ("PPI"), is typically between about 5 and 100, and will depend on the size of the flat wires as well as the size of the catheter. For flat wires of at least about 0.003" thick by about 0.007" wide and a catheter having an inner lumen of at least about 6 French, the PPI is preferably between about 10 and about 90, more preferably between about 10 and about 55. For example, the PPI for flat wires of about 0.003" thick by about 0.007" wide is preferably between about 20 and about 90, more preferably between about 35 and about 55 for an inner lumen of at least 6 French, and most preferably between about 35 and about 45 for an inner lumen of at least about 10 French. The PPI for flat wires of about 0.004" thick by about 0.012" wide is preferably between about 15 and about 70, and more preferably between about 15 and about 22 for an inner lumen of at least about 6 French. The PPI for flat wires of about 0.004" thick by about 0.020" wide is preferably between about 5 and about 50, and more preferably between about 10 and about 20 for an inner lumen of at least about 6 French, and most preferably between about 10 and about 20 for an inner lumen of at least about 16 French. Thus, as previously noted, the braid density may be non-varying or substantially consistent over the braiding length. Among other things, this enables the braid to be cut from anywhere on the reflow mandrel. For example, the braid can be pulled down tightly on a reflow mandrel to provide one substantially continuous PPI, or at least not intentionally varied. In these cases, placement or orientation on the mandrel is not an issue, resulting in less wasted braiding.

Alternatively, the torque transfer layer 1204 may utilize a varying braid density construction along the length of the introducer catheter 1200. For example, the torque transfer layer may be characterized by a first braid density at the proximal end of the introducer catheter 1200 and then transition to one or more braid densities as the torque transfer layer 1204 approaches the distal end of the introducer catheter 1200; the braid density of the distal end may be greater or less than the braid density at the proximal end. In one example, the braid density at the proximal end is about 50 PPI and the braid density at the distal end is about 10 PPI. In another embodiment, the braid density at the distal end is about 20-35% of the braid density at the proximal end. In another example, the braid density at the proximal end is about 20-35% of the braid density at the distal end.

The torque transfer layer 1204 may be formed separately on a mandrel or disposable core and subsequently slipped around the inner liner 1202. One or more portions of the torque transfer layer 1204 may be heat tempered and cooled before incorporation into the introducer body 1200 through methods that are known to those of ordinary skill in the art. The action of heat tempering may help to release the stress on the wire and help reduce radial forces. It is also contemplated that torque transfer layer 1204 may be braided directly on the inner liner 1202.

In one embodiment, a torque transfer layer 1204 comprises 0.003" by 0.007" 304 stainless steel wires at 35 PPI for an inner lumen of 6-10 French. Another representative torque transfer layer 1204 comprises 0.004" by 0.012" 304 stainless steel wires at 22 PPI for an inner lumen of 12 French. Yet another representative torque transfer layer 1204 comprises 0.004" by 0.020" 304 stainless steel wires at 13 PPI for an inner lumen of 16 French. These exemplary torque transfer layers may be manufactured on a commercially available horizontal braid machine utilizing a commercially available mandrel or disposable core. Other suitable methods of manufacturing the torque transfer layer 1204 will be apparent to those of ordinary skill in the art.

Figure 15:
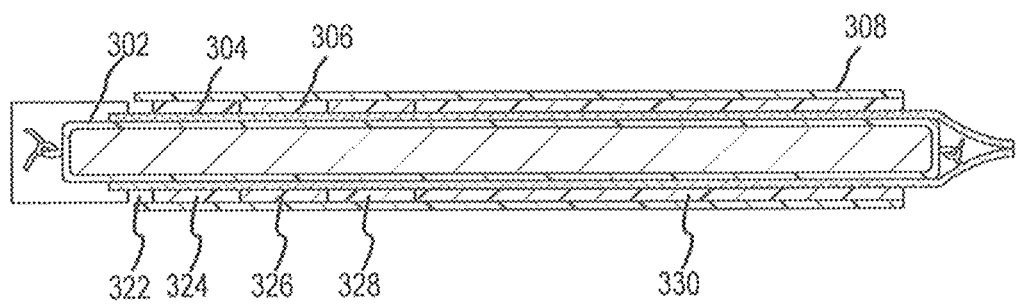
FIG. 15 depicts an outer sheath of varying components disposed over a torque transfer layer in accordance with a representative method of manufacture.

The outer sheath 1206 may be constructed of an extruded PEBAX or PTFE tubing. The melt-processing polymer of the outer sheath 1206 occupies a plurality of voids of the wire mesh in the torque transfer layer. The outer sheath 1206 may also be made of other melt processing polymers, including, without limitation, etched PTFE, polyether block amides, nylon and other thermoplastic elastomers, at varying durometers. The outer sheath 1206 may also comprise more than one layer, including, for example, two or more tubes of a melt processing polymer. Alternatively, as shown in FIG. 15, the outer sheath 306 may be comprised of varying segments 322, 324, 326, 328, 330 differing in hardness and/or material along the length of the introducer 300 and being reflow bonded together. This may be accomplished by layering or by placing annular rings of differing materials along the length of the introducer 300. Varying the sheath composition in this manner provides the additional benefit of adjusting flexibility, torqueability, and pushability at various points along the introducer 300.

In embodiments where the introducer is a steerable introducer (e.g., as shown in FIG. 11), at least one flat wire 1210 is provided, preferably extending along substantially the entire length of the introducer. The flat wire 1210 may be composed of stainless steel having dimensions of about 0.002"×about 0.016", or about 0.004"×about 0.012" or 0.016", or other dimensions. The flat wire may be selected such that the ratio of the width to thickness is at least about 2:1. In one embodiment, at least a portion of the flat wire is encased inside a preformed tube 1212 before placement along the inner liner 1202 to form a flat lumen 1214. The preformed tube 1212 need not be the same shape as the cross section of the flat wire, but instead, may be round, oval, rectangular, or another like shape. Preferably, the preformed tube 1212 has a cross section that is not the same shape as a cross section of the flat wire 1210, in order to facilitate movement of the flat wire in the preformed tube. The preformed tube may be formed of PTFE, etched PTFE, polyether block amides (such as PEBAX), nylon, other thermoplastic elastomers, or any other known material to one of ordinary skill in the art. In one embodiment, the preformed tube 1212 has a higher melting point than the outer sheath 1206 so that the preformed tube 1212 will not melt when the introducer catheter 1200 is subjected to melt processing. In alternative embodiments the flat wire 1210 may be covered with lubricious materials (not shown) before placement, including silicone and other lubricious materials. Alternatively, the flat wire 1210 may also be coated with a lubricious layer to promote slidability, and it is also contemplated that the flat wire 1210 may be manufactured with a smooth surface to promote slidability. While stainless steel is a preferred material to compose the flat wire 1210, other materials may be used, including, without limitation, materials that are used for conventional pull wires. More than one flat wire 1210 may also be used, and in such cases, each such flat wire 1210 may be encased inside its own flexible tube 1212. Preferably, as shown in FIG. 11, a pair of flat wires 1210 are used that are spaced at 180 degrees apart. The flat wires 1210 are preferably connected to at least one steering ring typically located near the distal end of the introducer (see, e.g., similar flat wires 30 connected to steering ring 90 in FIG. 2). The proximal ends of the flat wires 1210 are then operably connected to a steering mechanism (not shown) allowing for manipulation, or steering, of the introducer catheter 1200 during use.

Figure 12:
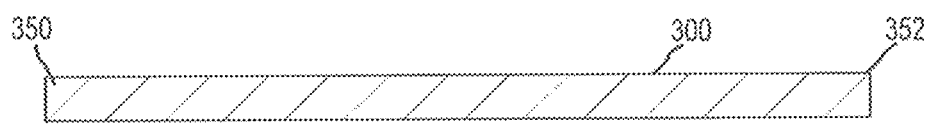
FIG. 12 depicts a reflow mandrel assembly used in the method of manufacturing introducers.
Figure 13:
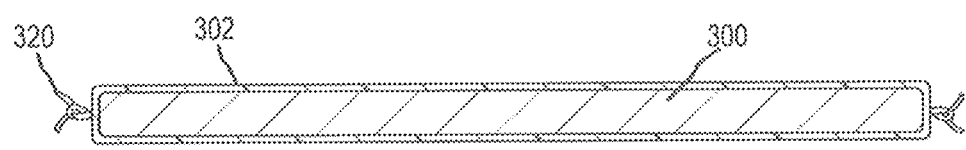
FIG. 13 depicts an inner layer disposed over a reflow mandrel assembly in accordance with one representative method of manufacture.

A representative method of manufacture is described in reference to FIGS. 12-18. As the various components are assembled, the introducer components may be collectively referred to as an introducer. As depicted in FIGS. 12-18, a mandrel 300 is depicted, which may be round in cross-section and may have a length ranging from about 6 inches to about 4 feet in length. Other shapes of mandrels may be used, depending on what medical device(s) is to be delivered via the lumen 1216. As depicted in FIG. 12, the mandrel 300 has a distal end 350 and a proximal end 352. As depicted in FIG. 13, an inner liner 302 is placed on the mandrel 300. The inner liner 302 is fed on to the mandrel 300 and in one embodiment is then knotted on one end 320, or both ends. In one embodiment, the inner liner 302 is a PTFE material.

Figure 14:
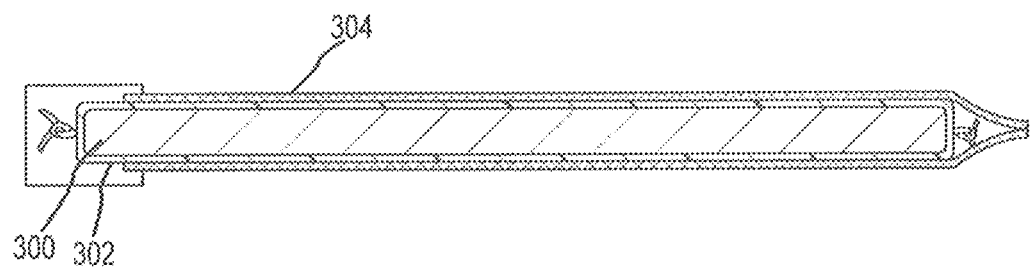
FIG. 14 depicts a torque transfer layer disposed over an inner layer in accordance with one representative method of manufacture.

As depicted in FIG. 14, a torque transfer layer 304 is then placed over the inner liner 302 in the illustrated embodiment. In the case of a steerable introducer catheter, the braided wire assembly (not shown) may then be placed over the torque transfer layer 304. Alternatively, the braided wire assembly may be placed over an outer sheath 306. Another sheath layer (not shown) may additionally be placed over the braided wire assembly. In one embodiment, the torque transfer layer terminates proximally of the distal end of the catheter.

Next, as depicted in FIG. 15, an outer sheath 306 is placed over the torque transfer layer 304 and may be made of either single or multiple sections of tubing that are either butted together or overlapped with each other. The multiple segments, or layers, of sheath material may be any length and/or hardness (durometer) allowing for flexibility of design. FIG. 15 identifies a plurality of segments, 322, 324, 326, 328 and 330. In this embodiment, the proximal end 330 of the outer sheath 306 may be made of a material such as nylon, and the remainder of the introducer may be made of one or more PEBAX materials. The lengths of the various segments may vary, but in one embodiment, the durometer hardness levels will decrease as the outer sheath 306 approaches its distal end. For example, a nylon base may then be followed by one or more of the following PEBAX segments: 72D PEBAX; 63D PEBAX; 55D PEBAX; 40D PEBAX; 35D PEBAX; 30D PEBAX. The introducer shaft may also use one or more blends of the foregoing PEBAX materials, including, for example, 70D/63D PEBAX blend made by co-extrusion, or a 40D/35D PEBAX blend made by co-extrusion, or a 72D/63D PEBAX blend made by co-extrusion. The various components of the outer sheath 306 according to this embodiment may be reflowed together during manufacturing. The proximal end of the shaft is the longest segment in one embodiment, and more distal segments may vary between, for example, 0.25" to 6", or from 0.25" to about 3", etc. The hardness levels of the segments and the lengths of the segments may be adjusted for specific applications, and in one embodiment the distal end may have the lowest durometer levels of all segments. The shaft segments may be selected to improve flexibility, torqueability, and pushability for the specific application, as appreciated by one of ordinary skill in the art. Alternatively, the introducer may be formed by placing a thin inner jacket or layer (e.g., PTFE layer) onto a mandrel (e.g., stainless steel mandrel) or extruding a thin inner jacket or layer (e.g., PEBAX layer) onto an extrusion mandrel (e.g., acetal mandrel), forming a torque transfer layer over the inner layer, and extruding an outer jacket or sheath (e.g., PEBAX jacket) over the torque transfer layer.

As noted above, PEBAX or similar material may be used rather than nylon 11 for the proximal shaft for purposes of flexibility. In another embodiment, an additional portion at or near the distal end is made from a lower durometer material than an adjacent portion proximal to this additional portion. For example, in one embodiment, an additional number of inches of a lower durometer PEBAX is provided at the distal end of the shaft for shaft compatibility when, for example, tracking through the heart to the left atrial appendage for safety concerns. Thus, in one embodiment, using different durometer configurations enables shaft integrity and steerability to be maintained throughout the shaft while having a softer flexible distal portion to prevent damage to the heart. In one particular example, the plurality of segments, 322, 324, 326, 328 and 330 of FIG. 15 may become more rigid with each segment moving in the proximal direction, whether the plurality of segments includes any two or more such segments. As a more particular example, two different segments may be used, such as segment 322 which is positioned adjacent to the main proximal shaft segment 330, such that segments 324, 326, 328 are not present. In this example, segment 322 may be made of a lower durometer material relative to the segment 330 (and/or other segment proximal to segment 322) to provide a softer flexible distal portion.

For purposes of example, one embodiment thus involves making a portion of the distal segment 322 of the outer sheath 306, such as the most distal six inches, from a lower durometer PEBAX or similar material. The lengths of the two or more segments may vary, but in one embodiment, the durometer hardness levels will decrease as the outer sheath 306 approaches its distal end. For example, PEBAX segments may include a decreasing durometer as the segments approach the distal end, such as ranging from 72D PEBAX through 30D PEBAX for segments 330 and 322 respectively, and intermediate segments 324, 326, etc. (if any) therebetween.

In one embodiment, a heat shrink layer 308 is placed over the assembled introducer assembly prior to reflow lamination. The heat shrink layer 308 may be a fluoropolymer or polyolefin material, such as FEP, or other suitable material as appreciated by one of ordinary skill in the art.

After assembly of the various components, the exemplary introducer assembly 300 is subjected to a reflow lamination process. FIG. 11 depicts a cross sectional view of the introducer assembly after this reflow process. Introducer assembly 1200 may be laminated by heating the assembly until the material comprising the outer sheath 1206 flows and redistributes around the circumference. Preferably, the heat shrink layer 1208 has a higher melt temperature than the outer sheath 1206, and during the melt process, the heat shrink layer 1208 retains its tubular shape and forces the liquefied sheath layer material 1206 into the torque transfer layer 1204 and into contact with the preformed tubes 1212 and the inner liner 1202. The introducer assembly 1200 may then be cooled. The mandrel is preferably left in place during the cooling process as it helps the introducer assembly to retain its inner lumen of, for example, at least about 6 French. The heat shrink layer 1208 may be left on the introducer assembly 1200, or optionally removed. If the heat shrink layer 1208 is removed, the outer sheath 1206 becomes the outside layer of the introducer catheter 1200.

Figure 16:
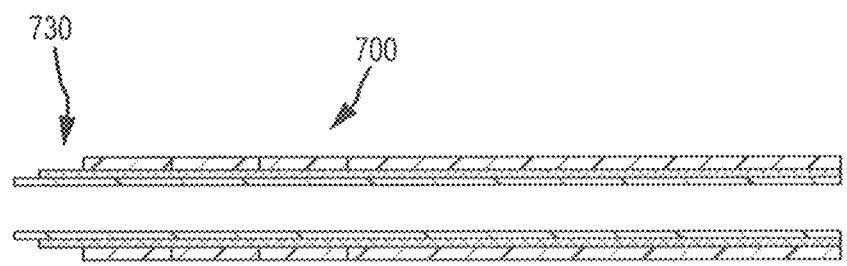
FIG. 16 depicts the components of an introducer assembled over a reflow mandrel assembly having a distal configuration for a tip assembly.
Figure 17:
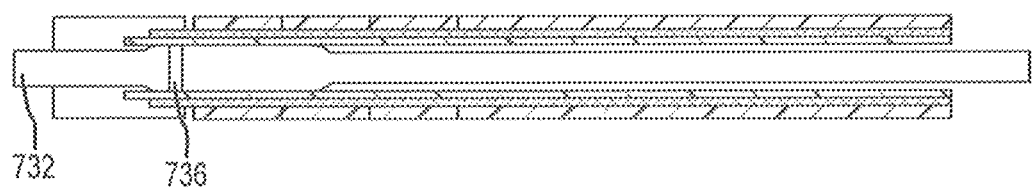
FIG. 17 depicts a tip component, having a radiopaque marker, attached to the distal end of the introducer depicted in FIG. 16.
Figure 18:
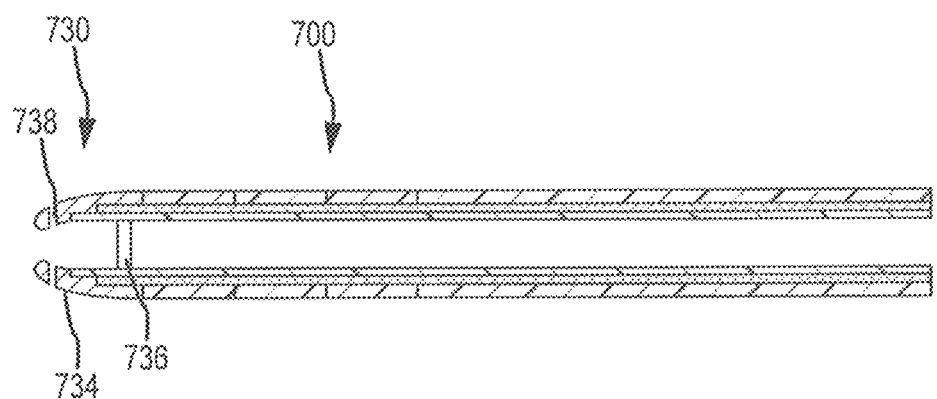
FIG. 18 depicts another tip component, having a radiopaque marker, attached to the distal end of the introducer depicted in FIG. 16.

Additionally, as shown in FIGS. 16-18, one embodiment contemplates the inclusion of a tip assembly for use in medical procedures, such as an atraumatic tip, including, for example, a radiopaque material contained therein for location of the tip during use. For example, FIGS. 16-18 depict a cross section of an introducer catheter 700 having a distal portion 730 configured to accept a tip assembly 732 or 734. In both examples, the tip 732 or 734 includes a ring 736, e.g., a radiopaque marker, for location of the tip 732 or 734 during use. Additionally, FIG. 18 further includes a tip assembly 734 configured with a plurality of port holes 738 for delivery of, for example, irrigation fluid. The tip assembly may further be configured with ablation electrodes (not shown) operably connected to a power supply (not shown), for use in cardiac ablation procedures.

Another representative method of manufacture is now described in connection with FIGS. 19A and 19B. The illustrated method of FIGS. 19A/B provides one example of a general method for manufacturing an introducer or other guiding medical device having particular characteristics, although additional, fewer and/or different method steps may be implemented in different embodiments. Further, the description below may be applied to other manufacturing methods described herein.

Figure 19A:
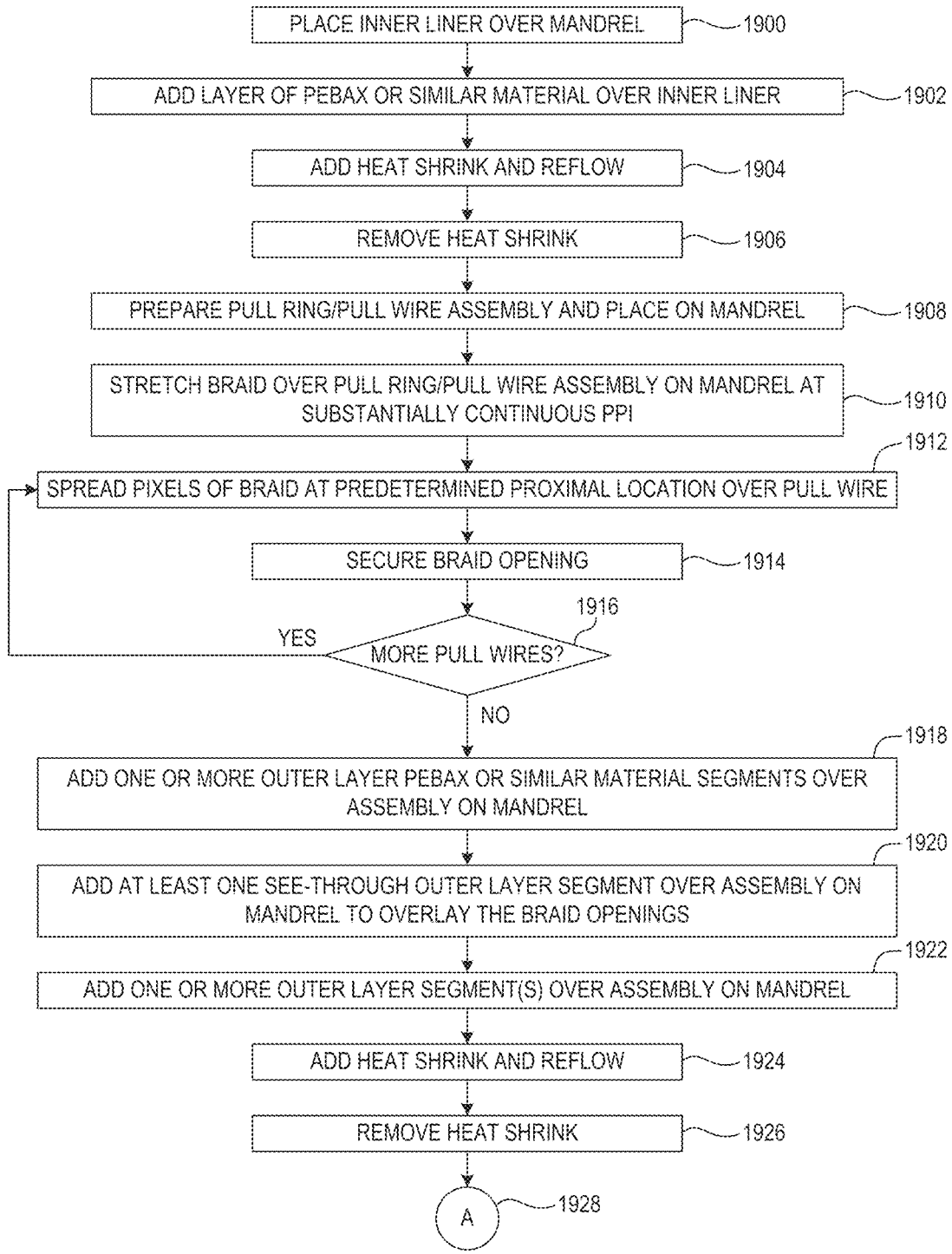
FIGS. 19A/19B depict a flow diagram of a representative method for manufacturing an introducer shaft in accordance with one embodiment.
Figure 20:
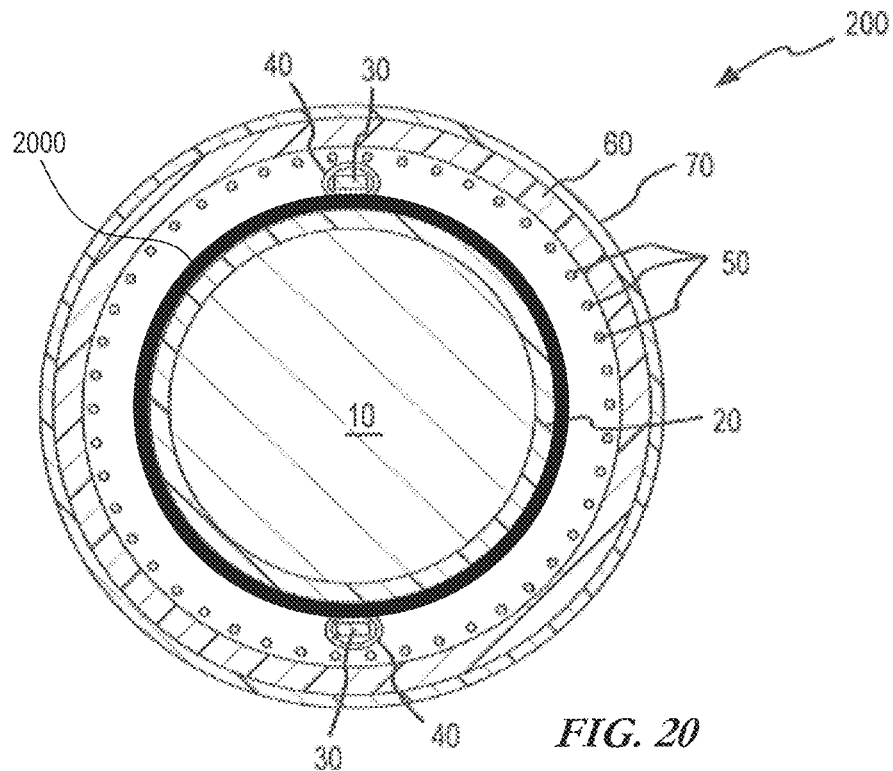
FIG. 20 is a representative cross-sectional view of an exemplary introducer assembly prior to the application of heat to melt process the outer layer.
Figure 21:
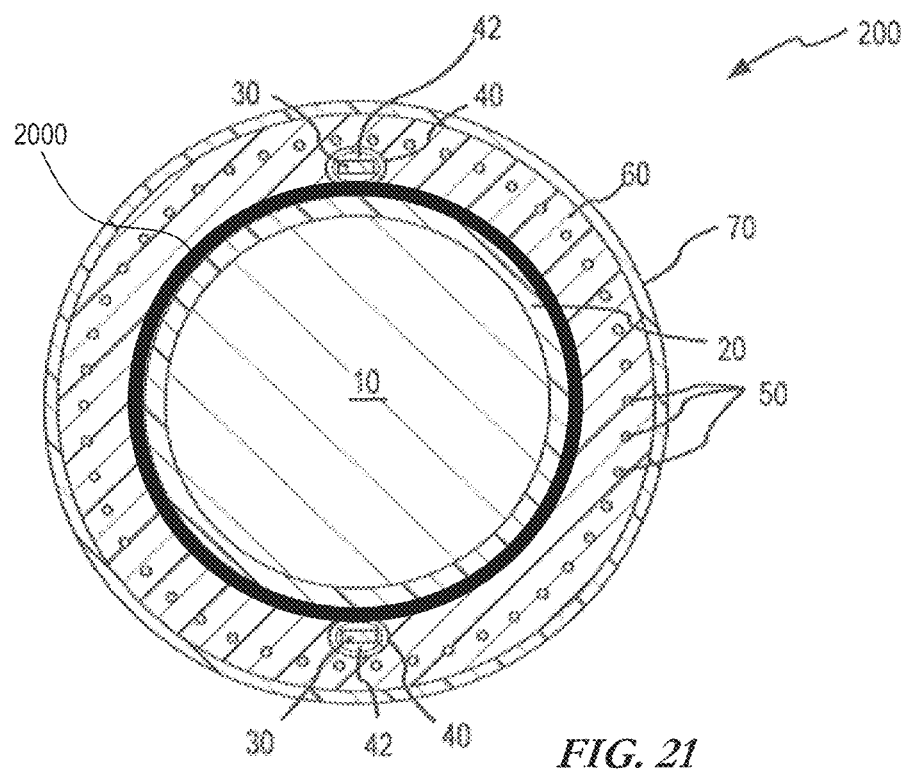
FIG. 21 is a representative cross-sectional view of an exemplary introducer after the application of heat to melt process the outer layer.

In the example of FIGS. 19A/B, an inner liner is placed 1900 on a mandrel 10. For example, a PTFE liner may be placed and stretched over a reflow mandrel 10. In one embodiment, a thin layer of PEBAX or analogous layer is added 1902 between the PTFE or other liner and outer layers (e.g., a braid). In one embodiment, this layer is added 1902 along the length of the mandrel 10, while in other embodiments it is added 1902 over some lesser portion of the mandrel 10. In one particular embodiment, the layer is added over the length of the mandrel 10, while in another embodiment the layer is added at least proximate where the pull wires (not yet added to the assembly) will exit the reflow shaft to attach to an introducer handle. In one particular embodiment, approximately two inches of 72 durometer PEBAX is slid over the proximal end of the reflow mandrel 10 and positioned at a location where the pull wires will exit the reflow shaft to attach to a introducer handle. In one embodiment, an introducer configured to deliver a left atrial appendage occluder is manufactured to add this layer of PEBAX between approximately 36.5 inches and 38.5 inches from the distal end. In such an embodiment, the pull wires will exit to the handle somewhere in this range where the underlying layer of PEBAX or other analogous material was added 1902. FIGS. 20 and 21 are respective cross-sectional views of an exemplary introducer assembly prior to and after the application of heat to melt process the outer layer. Using like reference numbers to those in FIGS. 6 and 7 for corresponding items, the layer of PEBAX or other material 2000 is depicted over the inner liner 20. The cross sectional area shown in FIGS. 20 and 21 corresponds to at least the portion proximate to the location where the pull wires will be extracted from the shaft assembly on the mandrel 10 or the reflowed shaft, as the case may be.

Returning to FIG. 19A, a layer of heat shrink may be added and reflowed via the addition of heat, as shown at block 1904. After sufficient cooling, the heat shrink layer may be removed 1906 after the PEBAX or other layer 2000 has been reflowed onto the assembly.

In one embodiment, the introducer is manufactured to be steerable, such as bi-directionally steerable. In the example of FIG. 19A/B, a pull ring and pull wire assembly is prepared and placed on the mandrel 10, as shown at block 1908. For example, the pull wires may be attached to the pull ring on substantially opposite sides of the pull ring in order to facilitate deflection in substantially opposite directions. In one particular embodiment, preformed tubes 40 are first placed over the pull wires up to a position at or near the pull ring, and this assembly is then pulled over an end (e.g., the distal end) of the reflow mandrel 10. In one embodiment, at least the pull ring area is reflowed at this time. Pull wires may then be properly aligned and retained in a desired position along the assembly.

One embodiment further involves utilizing a layer, such as braiding, shown in FIGS. 20 and 21 as braided wire assembly 50. The braid may be stretched 1910 over the pull ring/pull wire assembly on the mandrel 10, which in one embodiment is stretched to maintain a substantially constant or continuous PPI. A stop tube may be positioned over the distal end point of the braid wire assembly 50, such as approximately two inches from the distal end of the reflow mandrel 10, enabling the braid to be stretched 1910 and cut, tied off, or otherwise managed at the proximal end of the reflow mandrel 10. As previously noted, a continuous braid PPI may be used on the braid mandrel 10, thereby enabling the braid wire assembly 50 to be cut from anywhere on the reflow mandrel 10 or elsewhere. For example, the braid can be pulled down tightly on the reflow mandrel 10 to provide one continuous PPI, whereby orientation on the mandrel 10 is not an issue, less "scrap" may occur, etc.

As shown at block 1912, the braid may be spread at predetermined proximal locations corresponding to the location where the pull wires will be extracted from the assembly to ultimately attach to a handle, such as a handle having a steering mechanism to enable pulling of the pull wires to responsively deflect the distal end of the introducer. For each pull wire in which the braid is spread, the braid opening is secured 1914. In one embodiment, this is performed for each of the pull wires, as determined at block 1916, until the braid has been spread 1912 and secured 1914 for each of the pull wires being implemented on that particular shaft.

One or more materials are added to the mandrel 10 as shown at blocks 1918, 1920. For example, one or more outer layer PEBAX or similar material segments may be added 1918 over the mandrel 10. In one embodiment, multiple segments having different durometers may be added 1918 to allow the flexibility of the shaft to differ along the length of the shaft as desired.

In one embodiment, at least one transparent, clear, translucent or otherwise sufficiently "see-through" outer layer segment 80 is added 1920 along with one or more of the other outer layers added 1918. This see-through layer may be added 1920 at a position along the mandrel to correspond to where the braid openings were made to facilitate extraction of the pull wires for later attachment to the handle. One or more additional outer layer segments may optionally be added 1922 to abut this "window" created from the clear or at least see-through layer. In one embodiment, this window is created with natural PEBAX that is sufficiently clear so that the pull wires can, in a later step, be seen for ease of extraction of the end of the pull wires for attachment to the handle.

Figure 22:
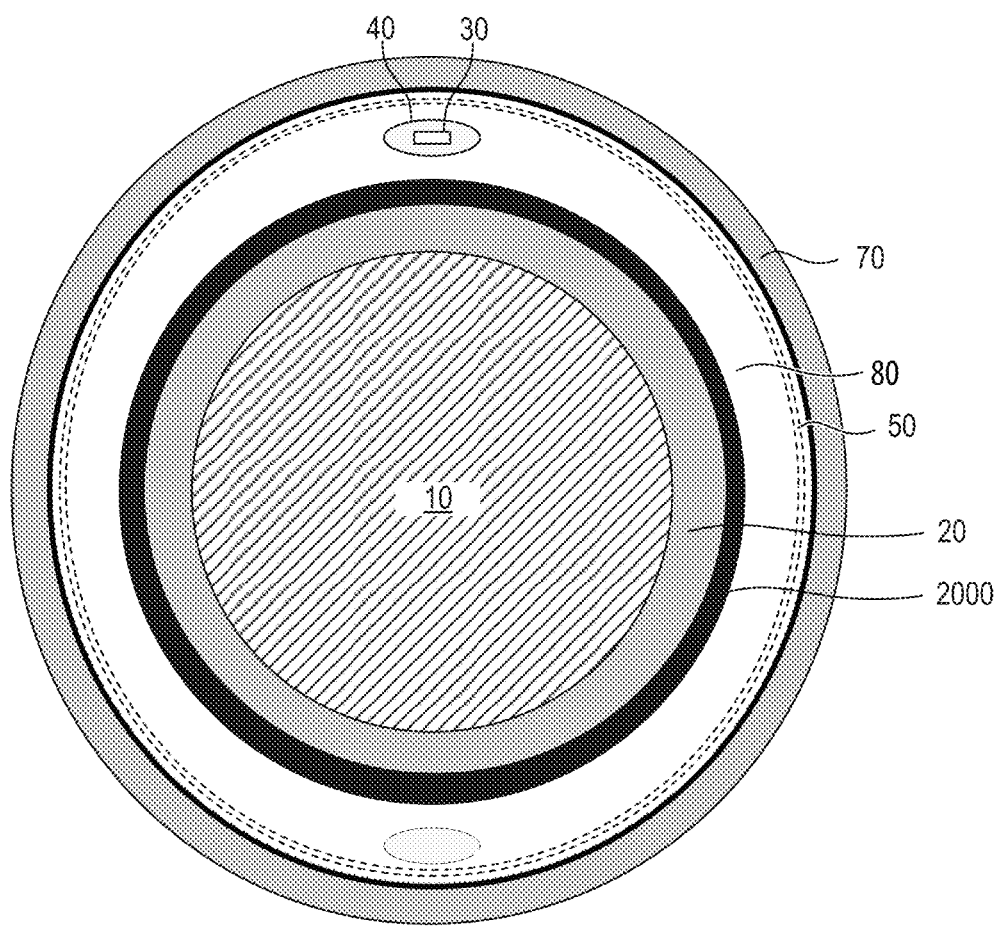
FIG. 22 is a representative cross-sectional view of an exemplary introducer assembly implementing a see-through outer layer proximate the pull wire extraction site.

An example of such a window is shown in FIG. 22. In this exemplary depiction, the cross sectional view is shown at a location commensurate with the placement of the see-through layer that was added at block 1920. A layer of heat shrink may be placed over any outer layers that have been added 1918, 1920, 1922, and reflowed, as depicted at block 1924. When the heat shrink layer 70 has been removed 1926, the preformed tube 40 and wire 30 are visible through the sufficiently clear outer layer 80. This facilitates extraction of the pull wires for connection to the handle (now shown), and reduces risk of leakage at the window/extraction site. It also optionally allows the pull wires to be pulled between the picks of the braid, thereby increasing structural integrity of the introducer at the pull wire site.

Figure 19B:
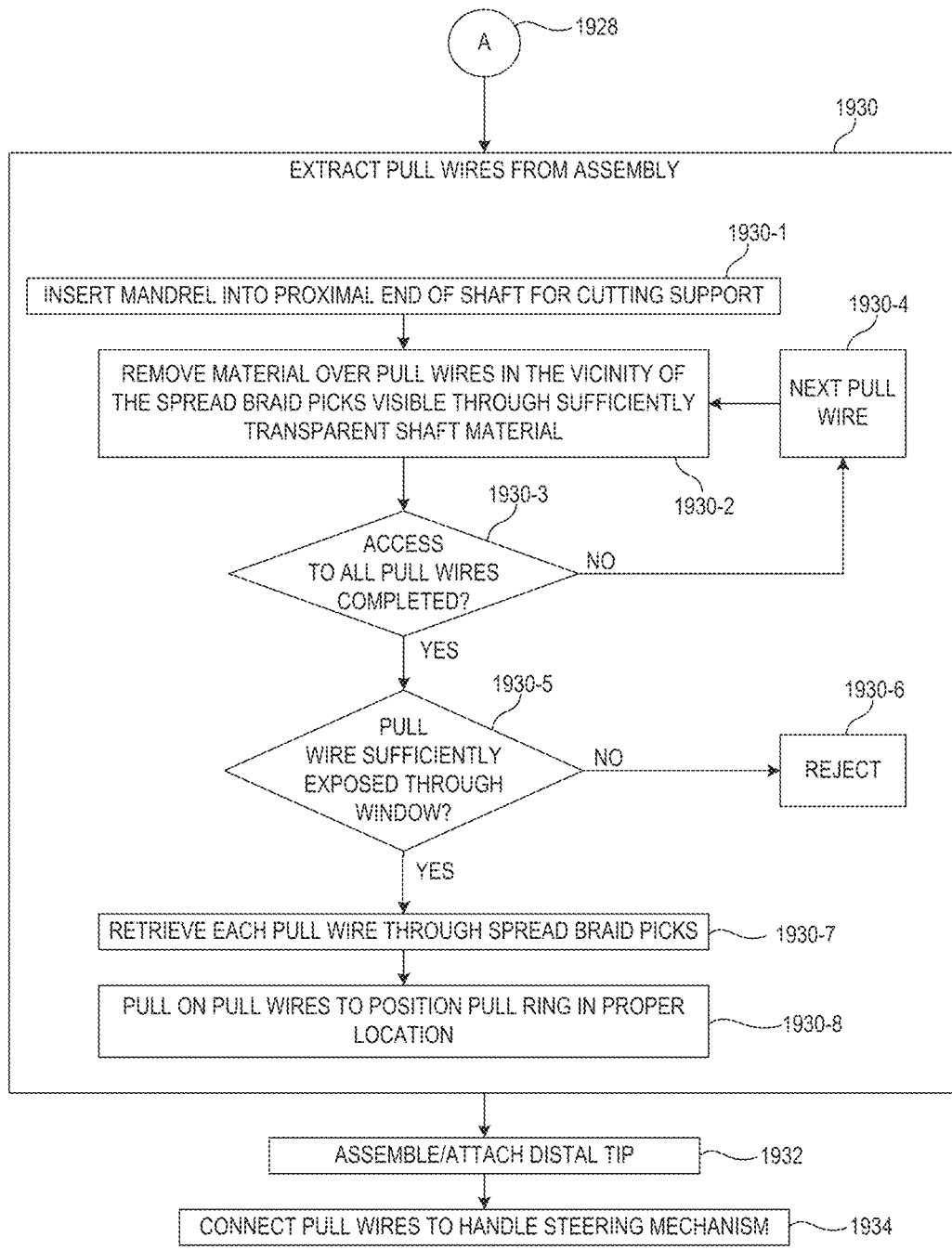

Connector 1928 continues the representative method at FIG. 19B, where the pull wires are extracted from the mandrel assembly. The extraction is accomplished with the assistance of the "see-through" outer layer that facilitates viewing and access to the pull wires for extraction and ultimate connection to the steering mechanism in the handle.

Block 1930 depicts one representative manner in which the pull wire(s) may be extracted from the mandrel assembly. This embodiment is described for purposes of example only, as other manners of accessing the pull wires using the transparent/translucent outer layer portion are contemplated. In this particular example, a cutting mandrel may be inserted 1930-1 into the proximal end of the shaft for cutting support in the window area. Thus, the cutting mandrel is inserted at least to, and preferably beyond, the position along the shaft in which the pull wires are located. The material (e.g., natural PEBAX) that is in the vicinity of the spread braid picks that reveal the pull wires is removed 1930-2 over the respective pull wire. This provides access to the pull wire. If access to all pull wires is not yet complete as determined at block 1930-3, the next pull wire 1930-4 is processed by removing 1930-2 that material.

When all pull wires have been processed in this fashion, it may be determined 1930-5 whether the pull wires are sufficiently exposed through the window. If not, the part may be rejected 1930-6, such as if the inner liner is cut or damaged, the pull wire is not exposed, etc. Otherwise, the pull wires are ready to be extracted.

In one embodiment, the pull ring may be pulled until the end of the pull wires are visible in the window, at which time each pull wire may be retrieved 1930-7 through the spread braid picks. A tool may be used to access each pull wire and pull the end out of the sheath assembly. The pull wires may then be pulled 1930-8 or otherwise manipulated in order to position the pull ring in a proper location. From this point, additional steps may be performed such as assembling/attaching 1932 a distal portion. For example, in one embodiment, a tip design may be used to deliver particular medical devices, such as including a tip design capable of delivering left atrial appendage ("LAA") occlusion devices and/or other devices. Still additional steps may include connecting 1934 pull wires to a handle steering mechanism, etc.

Among other things, this provides an improved process for getting pull wires out of the reflow shaft. The improved process includes any one or more of adding a layer, such as a thin layer of PEBAX, between the braid layer and the PTFE or other inner liner at least where the pull wires exit the reflow shaft to attach to the handle. The window is also reflowed with natural PEBAX or other suitable see-through material, to be clear enough so that the pull wires can be seen. Among other things, this reduces the risk of leak at the window site, and allows the pull wires to be pulled between the picks of the braid increasing the structural integrity of the introducer at the pull wire site.

Such methods enhance manufacturability of large bore introducers, as well as smaller bore introducers. In one embodiment, a large bore steerable sheath (approx. 12-14 French) is designed to improve the alignment with the LAA for delivering devices, such as LAA occluders (e.g., AMPLATZER™ Amulet™ device of St. Jude Medical), implantable structural heart devices, and the like. Among other things, the present disclosure describes a large bore steerable sheath large enough to deliver such devices.

Although several embodiments have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in claims created from this disclosure.

What is claimed is:

1. A method of manufacturing a catheter, comprising:
providing a mandrel;
placing a lining material over the mandrel to form an inner liner;
placing a thermoplastic elastomer layer over the inner liner and adjacent the inner liner, at least along the mandrel at a location where one or more pull wires will be extracted;
providing at least one pull wire;
placing a flexible liner over each of the at least one pull wires to create at least one lumen;
placing a braided wire assembly over the inner liner, the thermoplastic elastomer layer, and the at least one lumen, the braided wire assembly including at least two wires braided into a wire mesh;
providing pull wire access areas in the braided wire assembly;
covering the braided wire assembly with one or more melt processing polymers having decreasing durometers from proximal to distal end of the mandrel;
covering a portion of the braided wire assembly proximate the location where the one or more pull wires will be extracted with a melt processing polymer that is substantially see-through;
applying sufficient heat to the one or more melt processing polymers and the see-through melt processing polymer to raise the temperature of the polymer above its melting point;
cooling the assembly; and
removing the mandrel, thereby forming a catheter.

2. The method of claim 1, wherein the braided wire assembly is placed over the inner liner and the at least one lumen in a consistent braid pattern.

3. A method of manufacturing a catheter, comprising the steps of:
providing a mandrel;
placing a lining material over the mandrel to form an inner liner;
placing a thermoplastic elastomer layer over the inner liner and adjacent the inner liner;
providing at least one wire;
placing a flexible liner over each of the at least one wires to create at least one lumen;
placing a braided wire assembly over the inner liner, the thermoplastic elastomer layer, and the at least one lumen, the braided wire assembly including at least two wires braided into a wire mesh;
covering the braided wire assembly with one or more melt processing polymers having a durometer at the proximal end that differs from the durometer at the distal end of the mandrel;
applying sufficient heat to the melt processing polymers to raise the temperature of the polymer above their melting point;
cooling the assembly; and
removing the mandrel, thereby forming a catheter.

4. The method of claim 3, wherein the durometer at the distal end is greater than the durometer at the proximal end.

5. The method of claim 3, wherein the durometer at the distal end is less than the durometer at the proximal end.

6. The method of claim 3 further comprising the steps of:
covering a portion of the braided wire assembly proximate the location where the one or more pull wires will be extracted with a melt processing polymer that is substantially see-through;
applying sufficient heat to the one or more melt processing polymers and the see-through melt processing polymer to raise the temperature of the polymer above its melting point.

7. A method of manufacturing a catheter, comprising the steps of:
forming a tubular inner liner about a mandrel, the inner liner having a proximal end and a distal end, wherein the inner liner is polymeric;
placing a thermoplastic elastomer layer over the inner liner and adjacent the inner liner;
providing at least one pull wire;
forming a torque transfer layer over a portion of the liner and the thermoplastic elastomer layer, the torque transfer layer comprising a plurality of braided flat wires;
providing pull wire access areas in the torque transfer layer;
forming an outer sheath about the torque transfer layer, wherein the inner liner and the outer sheath define a catheter wall, and wherein the outer sheath comprises a melt-processing polymer;
covering a portion of the torque transfer layer proximate the location where the one or more pull wires will be extracted with a melt processing polymer that is substantially see-through;
applying sufficient heat to the melt processing polymer and the see-through melt processing polymer to raise the temperature of the polymer above its melting point
allowing the heated melt processing polymer and see-through melt processing polymer to cool until they each re-solidify; and
removing the mandrel.

8. The method of claim 7, wherein forming the torque transfer layer comprises:
   braiding the plurality of flat wires into a braided wire assembly at a braid density of between 10 PPI and 90 PPI.

9. The method of claim 7, wherein the outer sheath comprises a plurality of segments having different hardness characteristics joined together via a reflow bonding process.

\* \* \* \* \*